United States Patent [19]
Pang et al.

[11] Patent Number: 6,083,932
[45] Date of Patent: Jul. 4, 2000

[54] PHARMACEUTICAL COMPOSITIONS DERIVED FROM GINSENG AND METHODS OF TREATMENT USING SAME

[75] Inventors: Peter Pang; Jaqueline Shan; Brian Sloley; Christina Benishin; Bu Han Huang, all of Edmonton, Canada

[73] Assignee: CV Technologies Inc., Alberta, Canada

[21] Appl. No.: 09/061,961

[22] Filed: Apr. 17, 1998

Related U.S. Application Data

[60] Provisional application No. 60/044,464, Apr. 18, 1997, and provisional application No. 60/056,092, Aug. 28, 1997.

[51] Int. Cl.$^7$ .......................... A61K 31/715; A61K 31/58; A61K 35/78
[52] U.S. Cl. .............................. 514/54; 514/53; 514/169; 424/195.1
[58] Field of Search ........................... 424/195.1; 436/94; 514/54, 53, 169; 540/16

[56] References Cited

U.S. PATENT DOCUMENTS

| | | | |
|---|---|---|---|
| 4,157,894 | 6/1979 | Bombardelli | 436/94 |
| 5,137,878 | 8/1992 | Pang et al. | 514/54 |
| 5,230,889 | 7/1993 | Inoue | 424/195.1 |
| 5,589,182 | 12/1996 | Tashiro et al. | 424/423 |
| 5,668,154 | 9/1997 | Fink et al. | 514/338 |
| 5,776,460 | 7/1998 | Kim et al. | 424/195.1 |

OTHER PUBLICATIONS

Hou, J. P. The chemical constituents of ginseng plants. Comparative Medicine East and West, vol. V (2), pp. 123–145. (1977). No month found.

Battacharya et al. Anxiolytic activity of Panax ginseng roots: an experimental study. J. Ethnopharmacology 34, pp. 87–92. (1991). No month found.

Kim et al. Changes in chemical properties of red ginseng extract solution and physicochemical properties of precipitates formed during sterilization and storage. Koryo Insam Hakhoechi 20 (1), pp. 54–59. (1996). No month found.

Nabata et al. Pharmacological Studies of Neutral Saponins (GNS) of Panax Ginseng Root. Japan. J. Pharmacol. 23, pp. 29–41. (1973). No month given.

Schulten et al. Identification of Ginsenosides from Panax Ginseng in Fractions Obtained by High–Performance Liquid Chromatography by Field Desorption Mass Spectroscopy, Multiple Internal Reflection Infrared Spectroscopy and Thin Layer Chromatography. J. Chromatography. 212 (1), pp. 37–49. (Jul. 1981).

Benishin et al. Effects of Ginsenoside Rb1 on Central Cholinergic Metabolism. Pharmacology. 42, pp. 223–229. (1991). No month given.

Chepurnov et al. The Central Effects of Saponin Components and Polysaccharide Fractions form Korean Red Ginseng. Korean J. Ginseng Sci. 18 (3), pp. 165–174. (1994). No month given.

Chen, X. Cardiovascular Protection by Ginsenosides and their Nitric Oxide Releasing Action. Clinic. Exp. Pharmacol. Physiol. 23, pp. 728–732. (1996). No month found.

Salim et al. Ginsenoside Rb1 Regulates ChAT, NGF, and trkA mRNA Expression in the Rat Brain. Molec. Brain Res. 47(1–2), pp. 177–182. (Jul. 1997).

*Primary Examiner*—Michael P. Woodward
*Assistant Examiner*—Majorie A Moran
*Attorney, Agent, or Firm*—Arent Fox Kintner Plotkin Kahn

[57] ABSTRACT

Disclosed is a ginseng extract, HT1001, comprising a saponin fraction which is about 20–50% by weight of the ginseng extract. The extract is also described in terms of ultraviolet absorbance peak display and total ion count peaks display. Pharmaceutical compositions and methods of use for the extract for treating brain disorders, depression, and improving memory are also disclosed.

16 Claims, 33 Drawing Sheets

Fig.1

EXTRACTION OF HT-1001 FROM DRIED GROUND GINSENG ROOT

```
300 kg DRIED GROUND
GINSENG POWDER
```

FITZ MILL
MILL TO 80 MESH

EXTRACT ONCE IN FLAMMABLE REACTOR WITH 85% ETHANOL FOR 3 h, AT 90-95°C UNDER STIRRING.
(SOLID: SOLVENT RATIO = 1:8)
SEPARATE LIQUID AND SOLID PHASES WITH DECANTER CENTRIFUGE; 4200 rpm
USE 25 MICRON IN-LINE CARTRIDGE FILTER IN THE OUTPUT LINE

RESIDUE

POOLED SUPERNATANT

RECOVERED 85% ETHANOL

PROCESS B-LIQUID PHASE

B1  CONCENTRATE TO RECOVER ETHANOL; TARGET SOLID CONTENT
~10-12°(BRIX)
TEMP ~50°C, 15"Hg, AT FEED RATE OF 220-225 kg/h
CAUTION: WATCH FOR FOAMING
NOTE: MAY NEED TO ADD WATER TO AVOID THICKENING

CONCENTRATED EXTRACT

B2  SPRAY DRY @ FEED TEMP 42-58°C,
FEED RATE ~20 kg/h
150 TO 175°C INLET TEMP.
70 TO 90°C OUTLET TEMP.

DRIED EXTRACT

B3  MILL ANY LUMPS THAT MAY BE PRESENT USING FITZ MILL FITTED
WITH 0.065" SCREEN
BLEND

```
HT-1001
POWDER
```
~20% YIELD

Fig.25

GINSENG PROCESSING FLOW CHART

GROUND GINSENG 500g (HT-4001F)
↓ EXTRACT SAMPLE WITH 85% EtOH(1:8) IN A WATER BATH (95-100°C) FOR 3 HRS WITH CONTINUING AGITATION, THEN COOL SAMPLE DOWN TO ROOM TEMP AND POUR SUPERNATANT INTO A FLASK, IF NECESSARY, FILTER SUPERNATANT WITH A COTTON BALL AND A FUNNEL.

- RESIDUAL
- EtOH EXTRACTION
  ↓ REMOVE EtOH BY USING A ROTARY EVAPORATOR.

CONCENTRATED SUPERNATANT
↓ FREEZE DRY

HT-1001 POWDER OR CONCENTRATED SOLUTION
↓ ADD H2O TO CONCENTRATED SOLUTION UP TO 1L AND EXTRACT THE SAMPLE WITH 200ml ETHYL ACETATE FOR 3 TIMES, EACH TIME LET SAMPLE STAY IN RT FOR 3-4 HRS.

- AQUEOUS PHASE
  - EXTRACT WITH H2O SATURATED BUTANOL 200 ml FOR 4 TIMES AND STAY 3-4 HRS.
- ETHYL ACETATE PHASE
  - REMOVE ETHYL ACETATE AND DRY OILY MATERIAL, PQ6

- BUTANOL PHASE → TOTAL SAPONINS = PQ5
- AQUEOUS PHASE → OLIGOSACCHARIDE = PQ4

THE EFFECTS OF HT-1001, Rb1 AND Rg1 ON T-CALCIUM CURRENT IN N1E115 CELLS

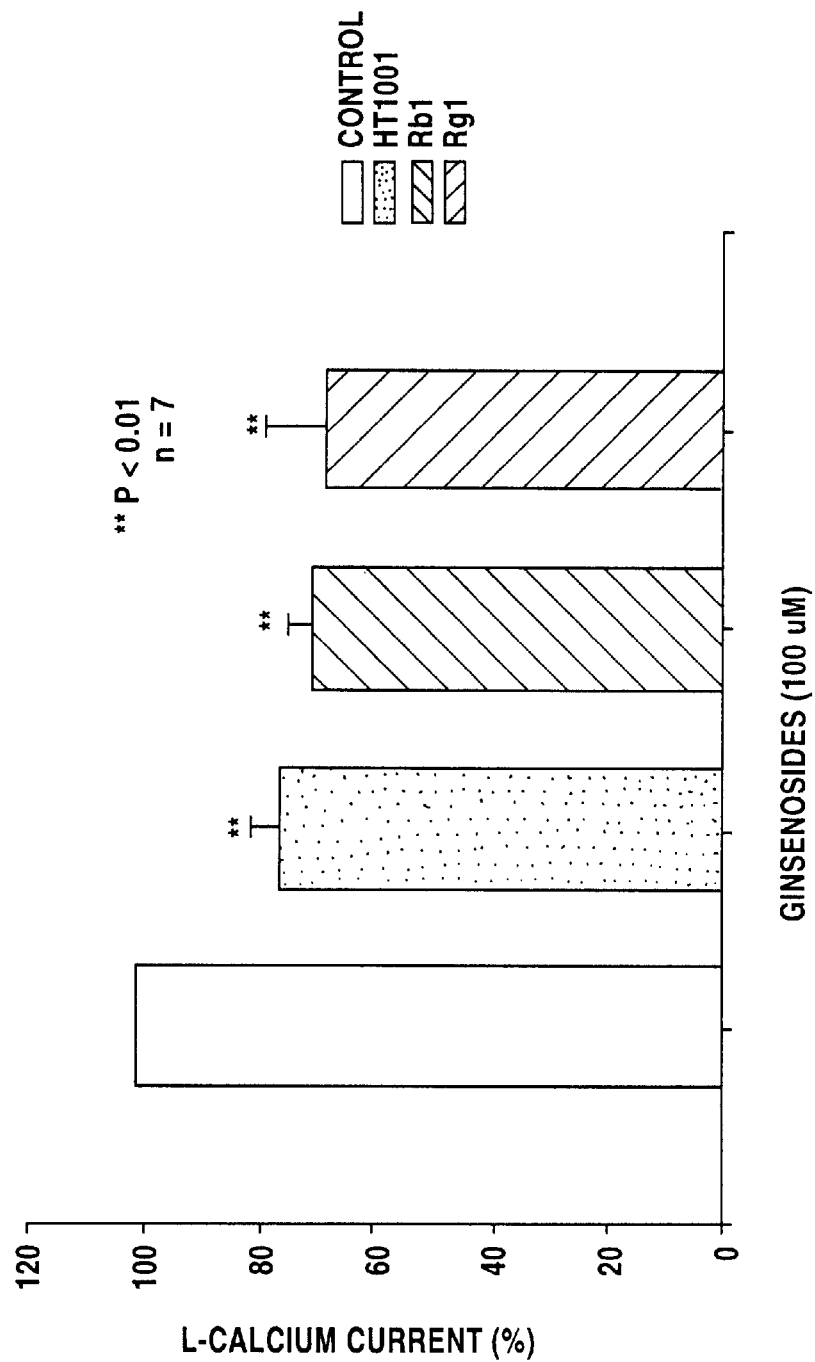

PHARMACEUTICAL COMPOSITIONS DERIVED FROM GINSENG AND METHODS OF TREATMENT USING SAME

This application claims the benefit of U.S. Provisional Application No. 60/044,464, filed Apr. 18, 1997, and U.S. Provisional Application No. 60/056,092, filed Aug. 28, 1997.

BACKGROUND OF THE INVENTION

The present invention is directed to pharmaceutical compositions derived from ginseng and methods of treatment for a variety of brain conditions or illnesses, as well as use for depression or general cognitive improvement.

Brain conditions such as senile dementia, Alzheimer's disease, Parkinson's disease, attention deficit disorder (ADD), mental retardation, stroke and other neurodegenerative diseases and conditions are widely recognized as problems of increasing proportions in North America, as well as around the world. Brain conditions such as these are associated with progressive physical and mental impairment to the point where the patient requires total care, and becomes a tremendous social and economic burden. Pathological studies of certain diseases, for example Alzheimer's disease, indicate that brains of certain patients have lost several neurotransmitter systems related to different functions. However, the system which is implicated the most is the cholinergic system. Studies show that several important cholinergic tracts innervating the cortical and hippocampal regions degenerate. Although this particular degeneration may not account for all symptoms of these several brain conditions, it may account for the cognitive and memory deficits.

The pharmacological approaches for the management of brain diseases affecting the cholinergic system may be classified in two ways. The first is drugs which improve the function of existing neurons, especially to increase cholinergic nerve function. The second is drugs which decrease degeneration and/or increase regeneration of nerves. It is generally believed that compounds which will increase the availability of the existing endogenous neurotransmitter acetylcholine (ACh) are desirable. In addition, compounds which prevent the age related increase in intracellular calcium would be expected to decrease neuronal degeneration. Furthermore, compounds which promote neuronal growth would be expected to ameliorate the cognitive deficits associated with age related neuronal degeneration.

Ginseng is the name given to the dried roots of the ginseng plants (genus Panax) and, more particularly, to extracts of those roots. The roots and their extracts contain a variety of substances including saponins and sapogenins.

Ginseng has been extensively used, mostly in Asia, as a tonic to promote health and well being, and as a medicine in the treatment of various disease conditions. The beneficial attributes of ginseng are attributed to its saponin content, a mixture of dammarane triterpene glucosides referred to collectively as ginsenosides. Some ginsenosides have been isolated, and their structure determined. Such ginsenosides include Rb1, Rb2, Rc, Rd, Re, Rf and Rg (see U.S. Pat. No. 4,157,894 to Bombardelli).

U.S. Pat. No. 5,137,878 to Pang et al contains a discussion of prior art extracts. The complete disclosure of U.S. Pat. No. 5,137,878 is hereby incorporated by reference in this application. U.S. Pat. No. 5,137,878 discloses that ginsenosides Rb1 and Rg1 enhance the availability of ACh in the cortical and hippocampal regions of the brain and alleviate the symptoms of Alzheimer-type senile dementia. The patent also discloses a process for isolating ginsenoside Rb1.

SUMMARY OF THE INVENTION

The present inventors have now discovered that administration of a specific ginseng extract, which the inventors have called HT1001 containing about 20–50%, preferably about 25–40%, total ginsenosides (a.k.a. saponins), is as effective as administration of either a single pure ginsenoside alone, or administration of an extract containing 100% of total ginsenosides. Therefore, the present invention is directed to the HT1001 extract, as well as pharmaceutical compositions containing the extract. The present invention is also directed to a method of treating a brain condition in a patient in need thereof, comprising administering to the patient a brain condition treating-effective amount of the HT1001 extract. The brain condition can, for example, be senile dementia, Alzheimer's disease, Parkinson's disease, attention deficit disorder, mental retardation or stroke.

Also included in the invention is a method of treating depression in a patient in need thereof, comprising administering to the patient a depression treating-effective amount of the HT1001 extract.

A method of improving learning ability or memory in a patient in need thereof is also disclosed, comprising administering to the patient a learning ability or memory improving-effective amount of the HT1001 extract.

BRIEF DESCRIPTION OF THE DRAWINGS

FIG. 1 shows a preferred extraction procedure for HT1001.

FIG. 25 is a description of the process used to produce HT1001 fractions PQ4, PQ5 and PQ6.

FIGS. 32 and 33 show the effects of HT1001 on calcium channel currents.

DESCRIPTION OF THE PREFERRED EMBODIMENTS

Figure 2:
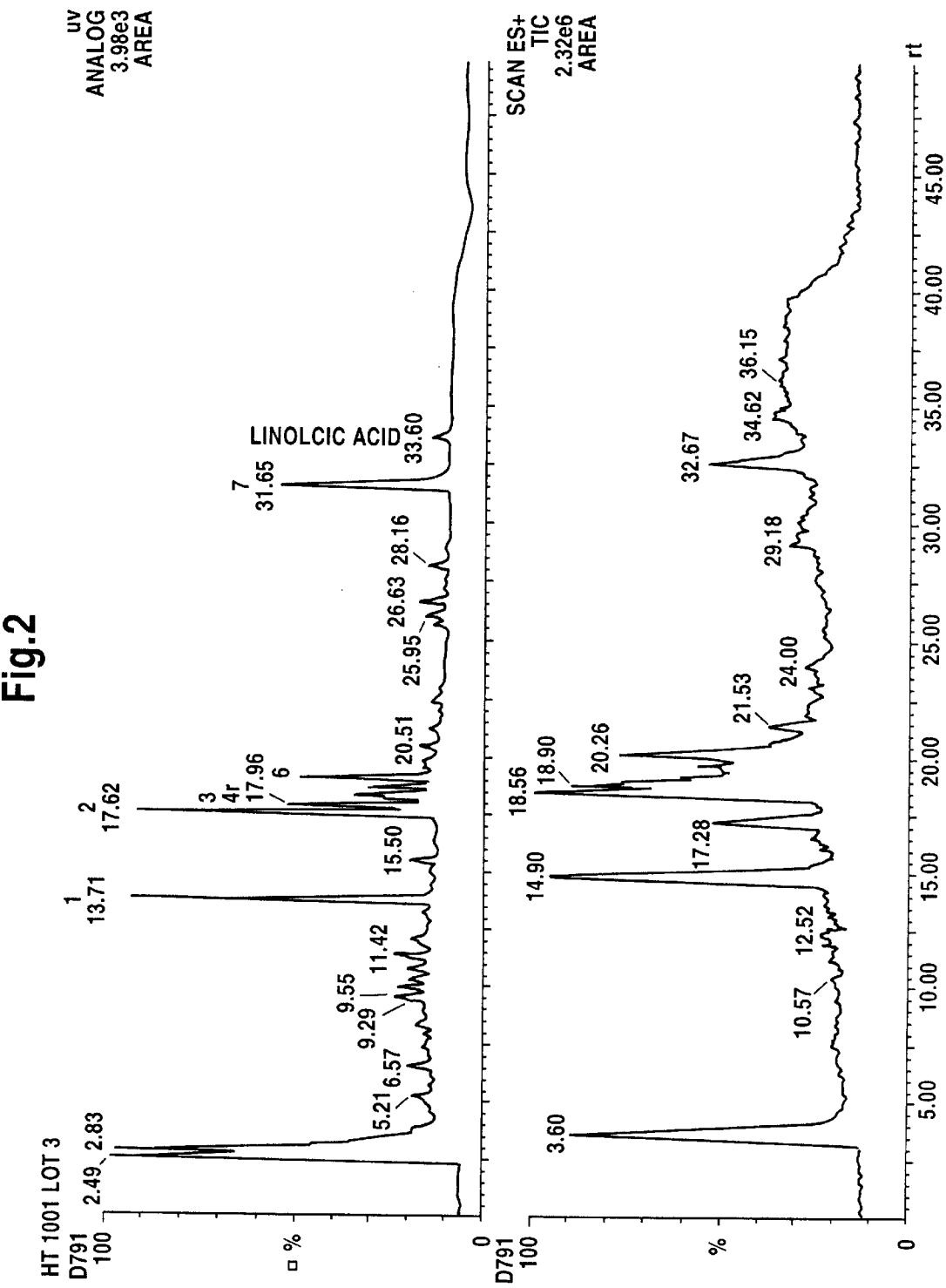
FIGS. 2 and 3 provide ultraviolet absorbance characteristics and total ion counts for HT1001 lots 3 and 4.

A preferred extraction process for HT1001 is as follows. 300 kg of dried ground ginseng powder is used as a starting material. If desired, the ginseng can be placed into a Fitz mill and milled to about 80 mesh. The ginseng is then subjected to an extraction process using ethanol. It is preferred that 85% ethanol be used, though modification is well within the ordinary skill of a worker in the art. A solid:solvent ratio of about 1:5 to 1:10 is suitable, however 1:8 is preferred. Extraction can proceed for about 1 to 5 hours, as necessary. The preferred extraction time is 3 hours. Extraction temperature can be in a range of from 80–105° C., but 90–95° C. is preferred. Stirring is recommended. The liquid and solid phases are preferably separated with a decanter centrifuge at a speed of about 4200 rpm using a 25 micron in-line cartridge filter in the output line.

If a number of extractions are done, the supernatants can be pooled. At any rate, the supernatant is subjected to a concentration step to recover the ethanol. A vacuum distillation process is preferred. The target solid content is about 10–12° (Brix). The temperature is preferably about 50° C., at 15" Hg, at a feed rate of 220–225 kg/h. Water may have to be added to avoid thickening.

The concentrated extract can be freeze, oven, drum and is preferably spray dried at a feed temperature of about 42–58° C. and a feed rate of about 20 kg/h. The inlet temperature is preferably about 150–175° C., and the outlet temperature is preferably about 70–90° C. Once dried, the extract may be milled, if desired, to eliminate any lumps that may be present. It is preferred to use a Fitz mill fitted with a 0.065" screen. The extract is then blended to produce a yield of about 20%. A diagram showing the preferred extraction procedure is attached as FIG. 1.

A chemical fingerprinting of HT1001 was conducted. Two lots of HT1001 were examined and a chemical fingerprint generated using high performance liquid chromatography coupled to ultraviolet absorbance detection and electrospray mass spectrometry.

10 mg of lot 3 and lot 4 of our HT1001 product were dissolved in 1.0 ml of 5% acetonitrile in water with 0.05% trifluoroacetic acid as a counter ion. This provided stock for characterization.

100 µl of the stock representing 1 mg original material was applied to the high performance liquid chromatographic (HPLC) system. The chromatographic system consisted of a Hewlett Packard 1050 gradient HPLC system equipped with an autoinjector and ultraviolet absorbance detector. The column consisted of a Zorbax 300SB-C8 reverse phase column (4.6 mm×25 cm).

The separation was achieved using a gradient elution using water, acetonitrile and trifluoroacetic acid. Mobile phase A consisted of 5% acetonitrile in water with 0.05% trifluoroacetic acid as counter ion. Mobile phase B consisted of 70% acetonitrile in water with 0.05% trifluoroacetic acid as counter ion. Flow rate was 1.0 ml/minute. At time=0 minutes the mobile phase consisted of 100% A. At 30 minutes the mobile phase was 100% B and between 0 and 30 minutes the gradient change was linear. Between 30 and 35 minutes the mobile phase was 100% B. Between 35 minutes and 40 minutes the mobile phase returned to 100% A from 100% B. A minimum 10 minute wash period in 100% A was performed prior to another injection. Ultraviolet absorbance was monitored at 203 or 205 nm.

Electrospray mass spectroscopy was performed using a Fisons Instruments VG Quatro instrument. Following elution from the ultraviolet absorbance detector the flow from the HPLC equipment was split and 2% (20 µl/minute) was fed into the electrospray instrument. Chemicals eluting from the HPLC instrument were monitored in positive mode for mass between 200 and 1200 molecular weight. A number of chemicals provided mass spectra characteristic of this product.

Figure 3:
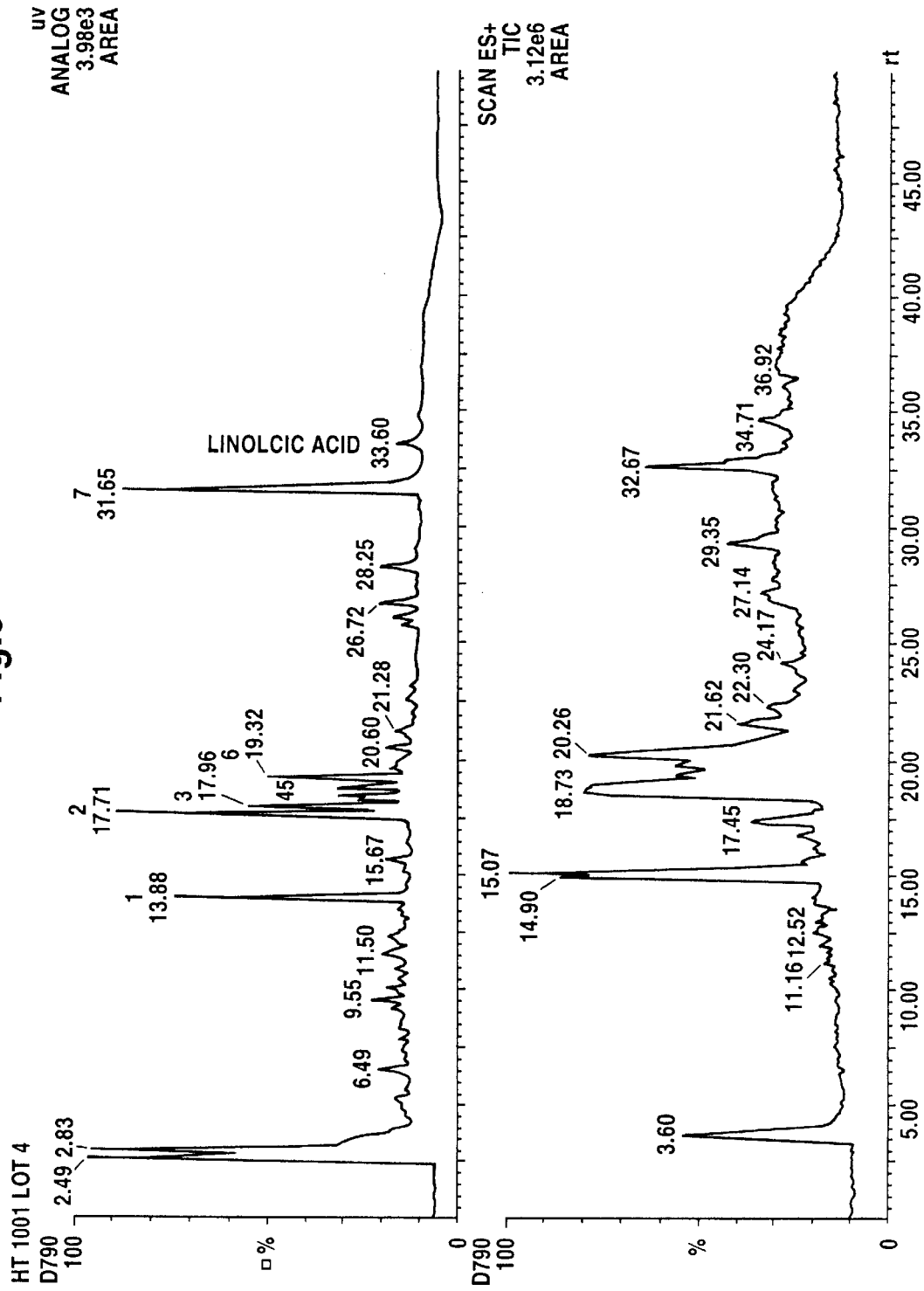
Figure 4:
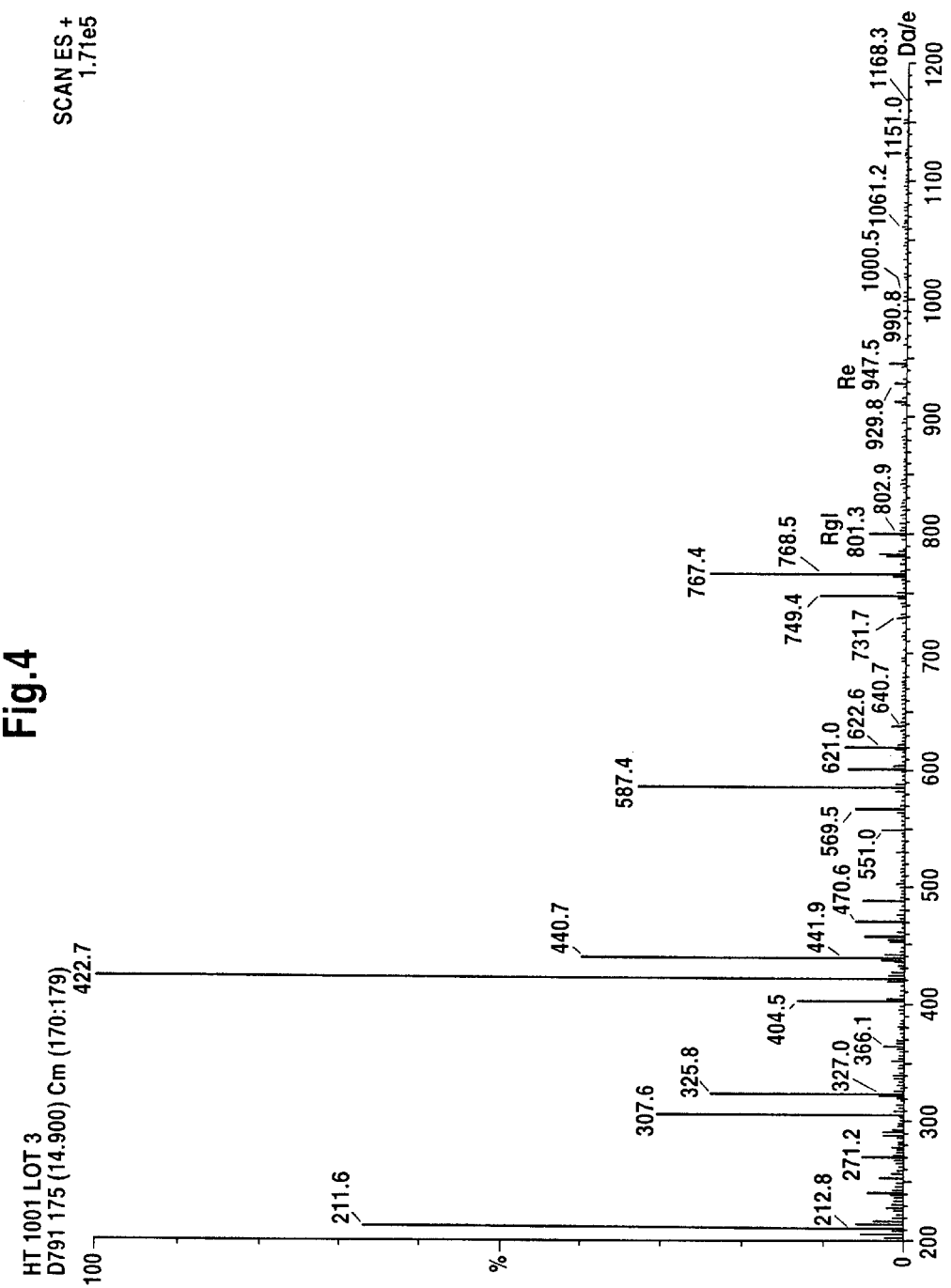
FIGS. 4–14 show mass spectra obtained from the seven prominent peaks in HT1001 lots 3 and 4.
Figure 5:
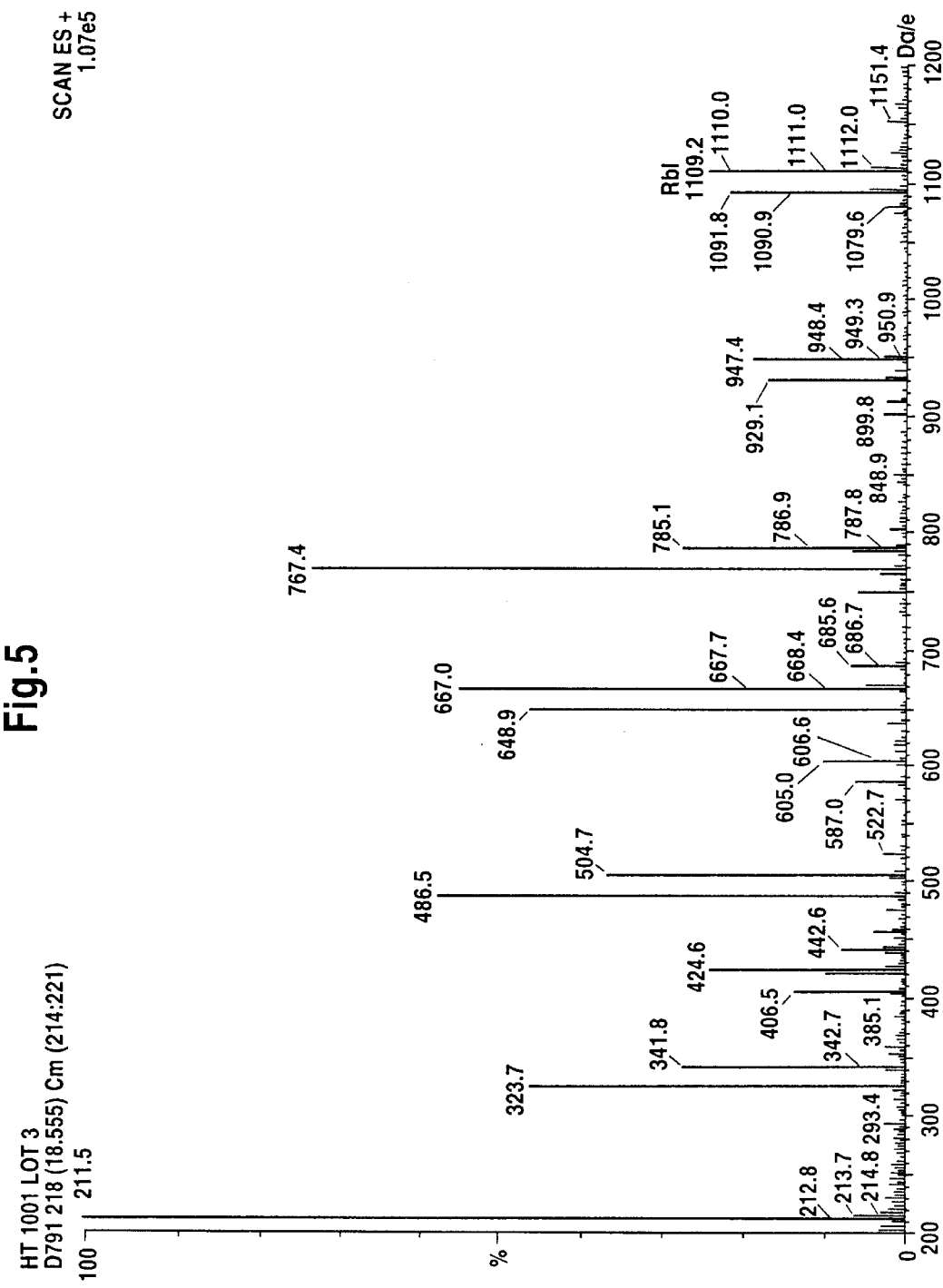
Figure 6:
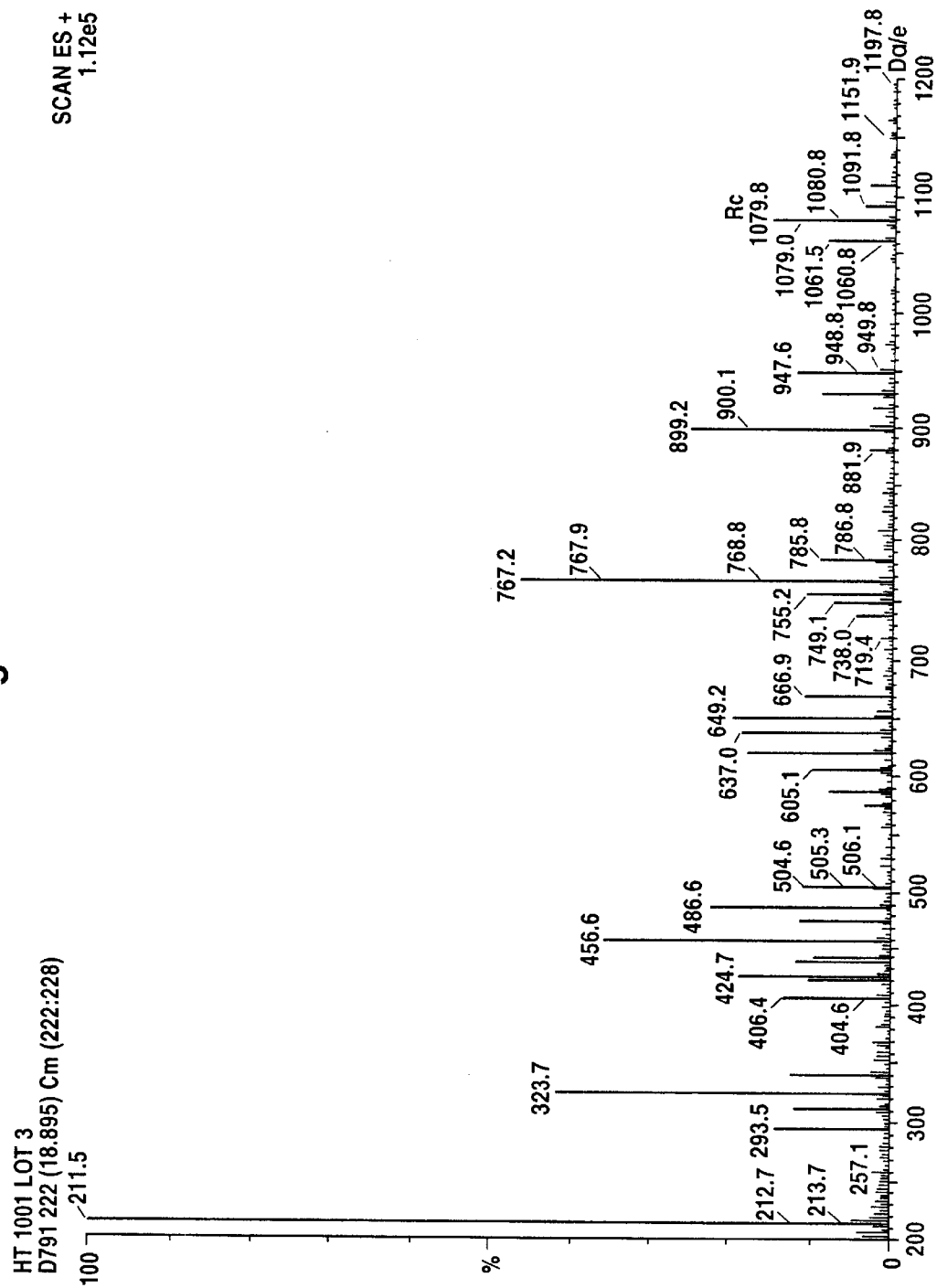
Figure 7:
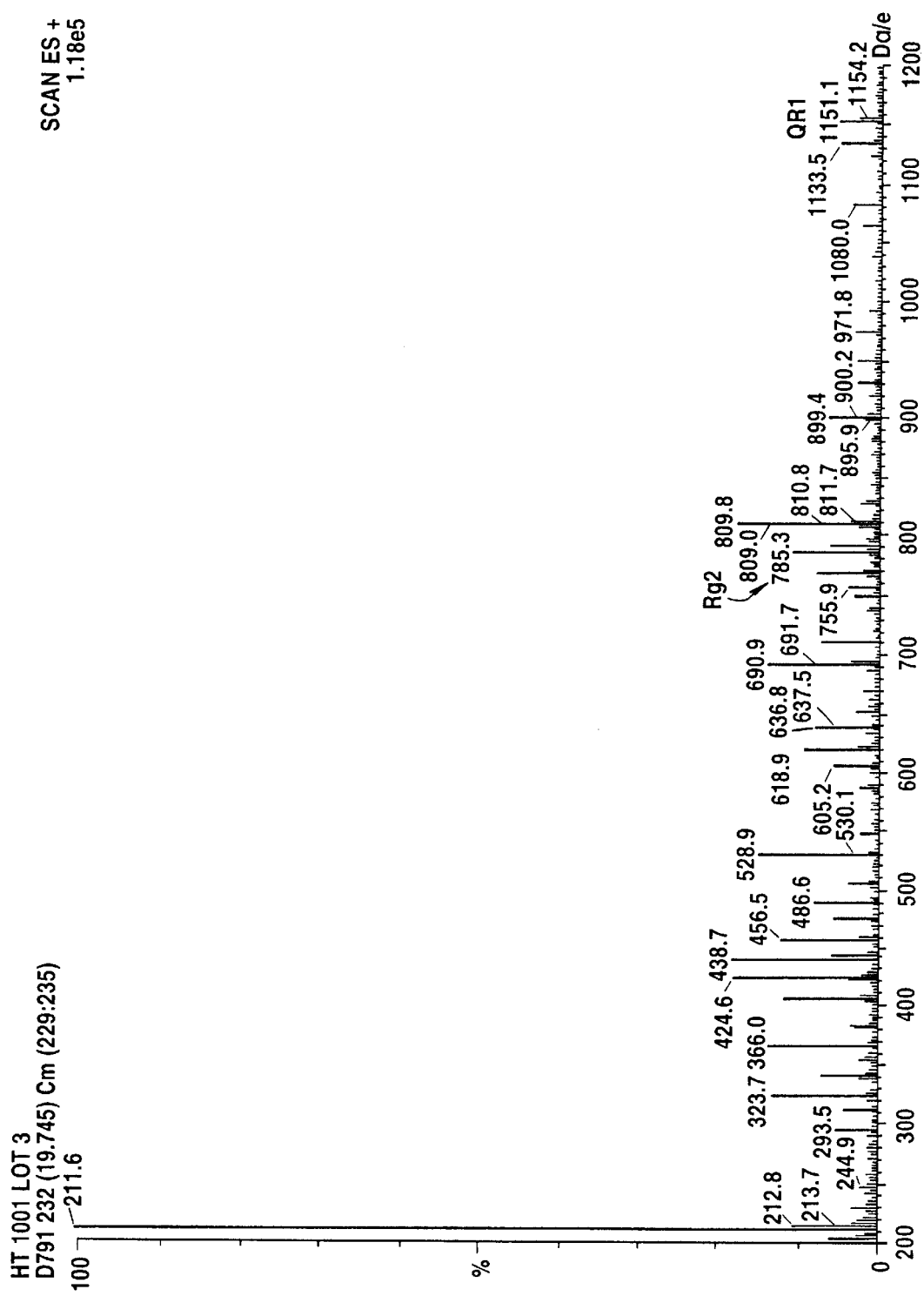
Figure 8:
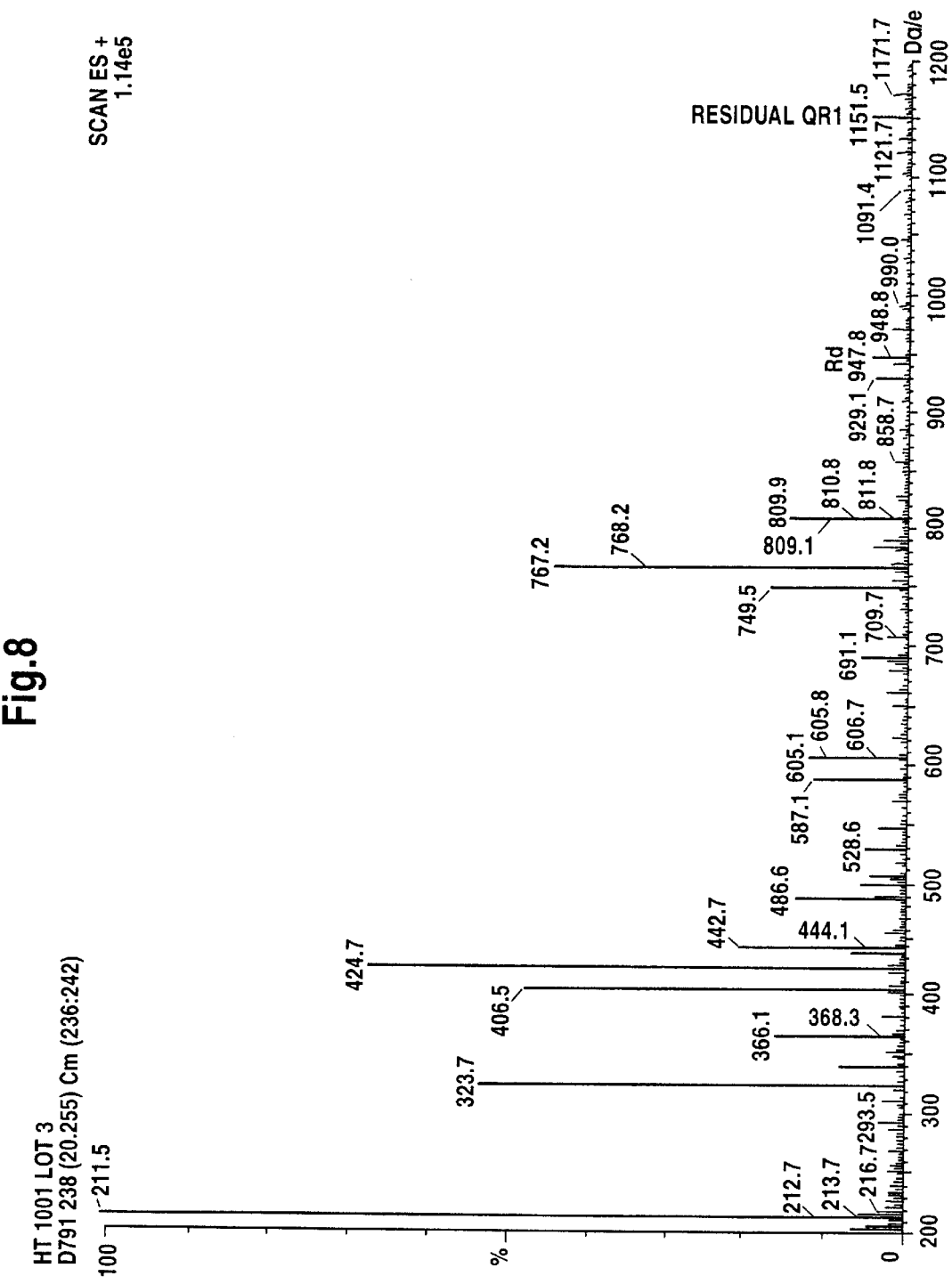
Figure 9:
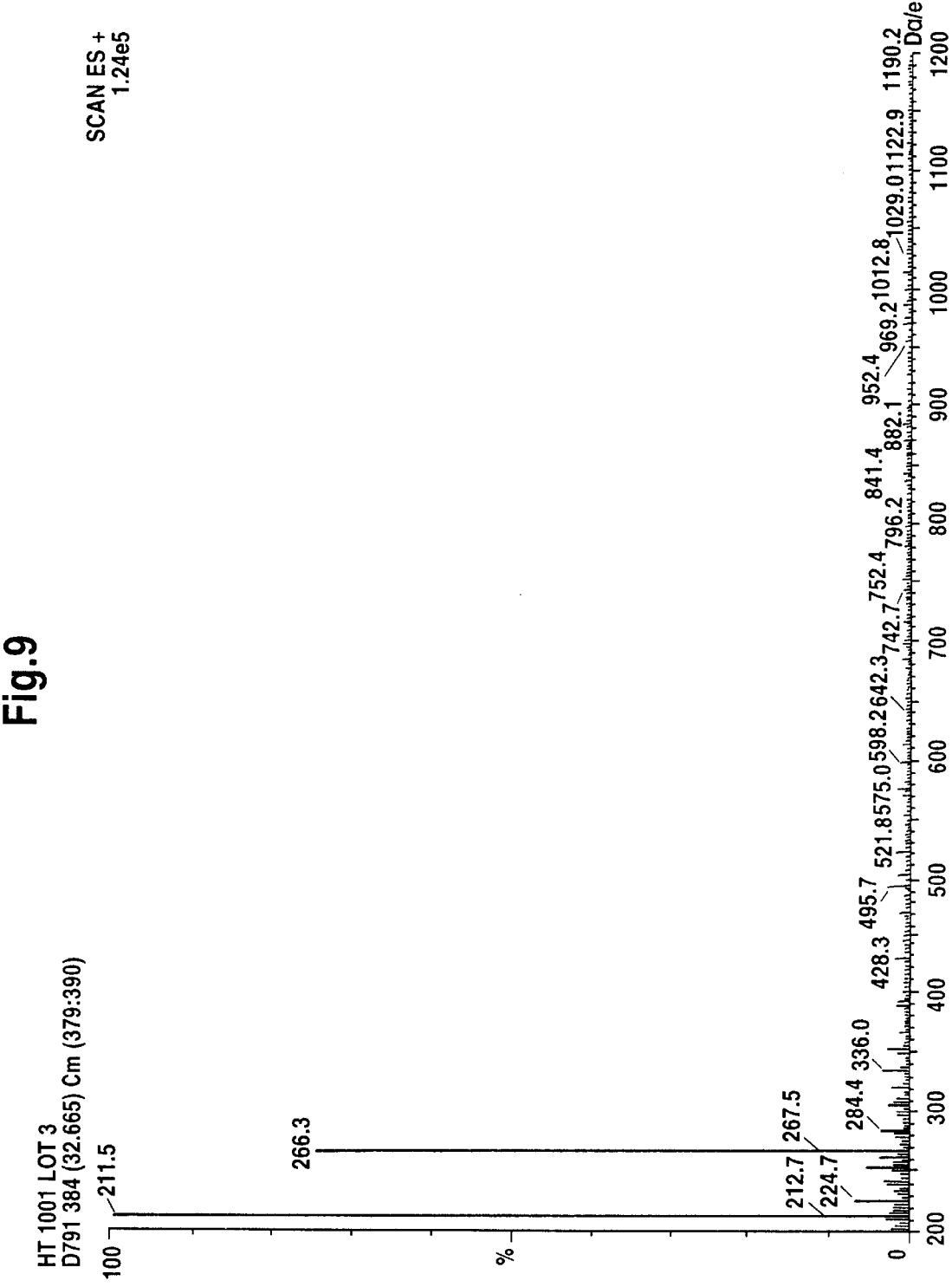
Figure 10:
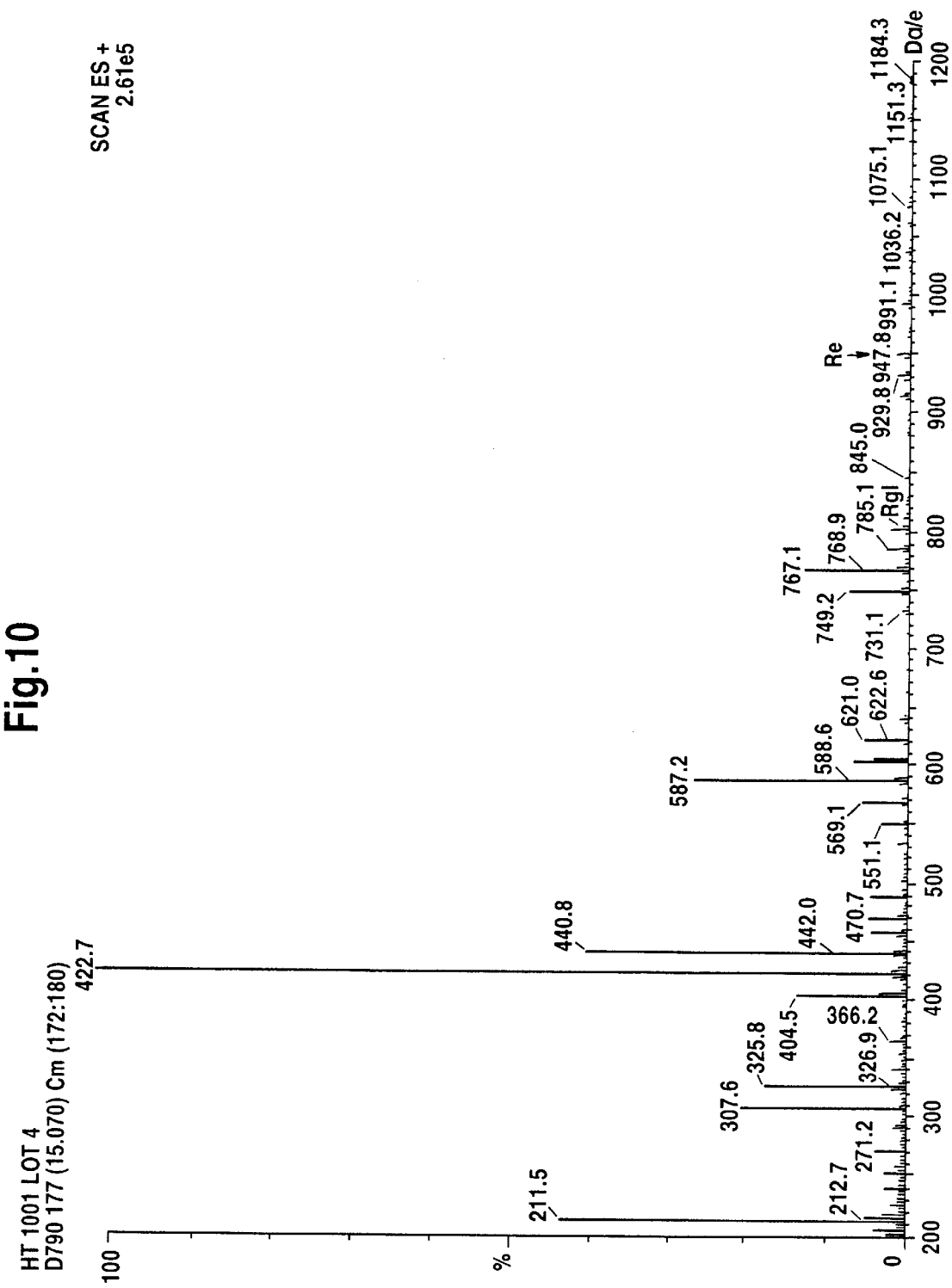
Figure 11:
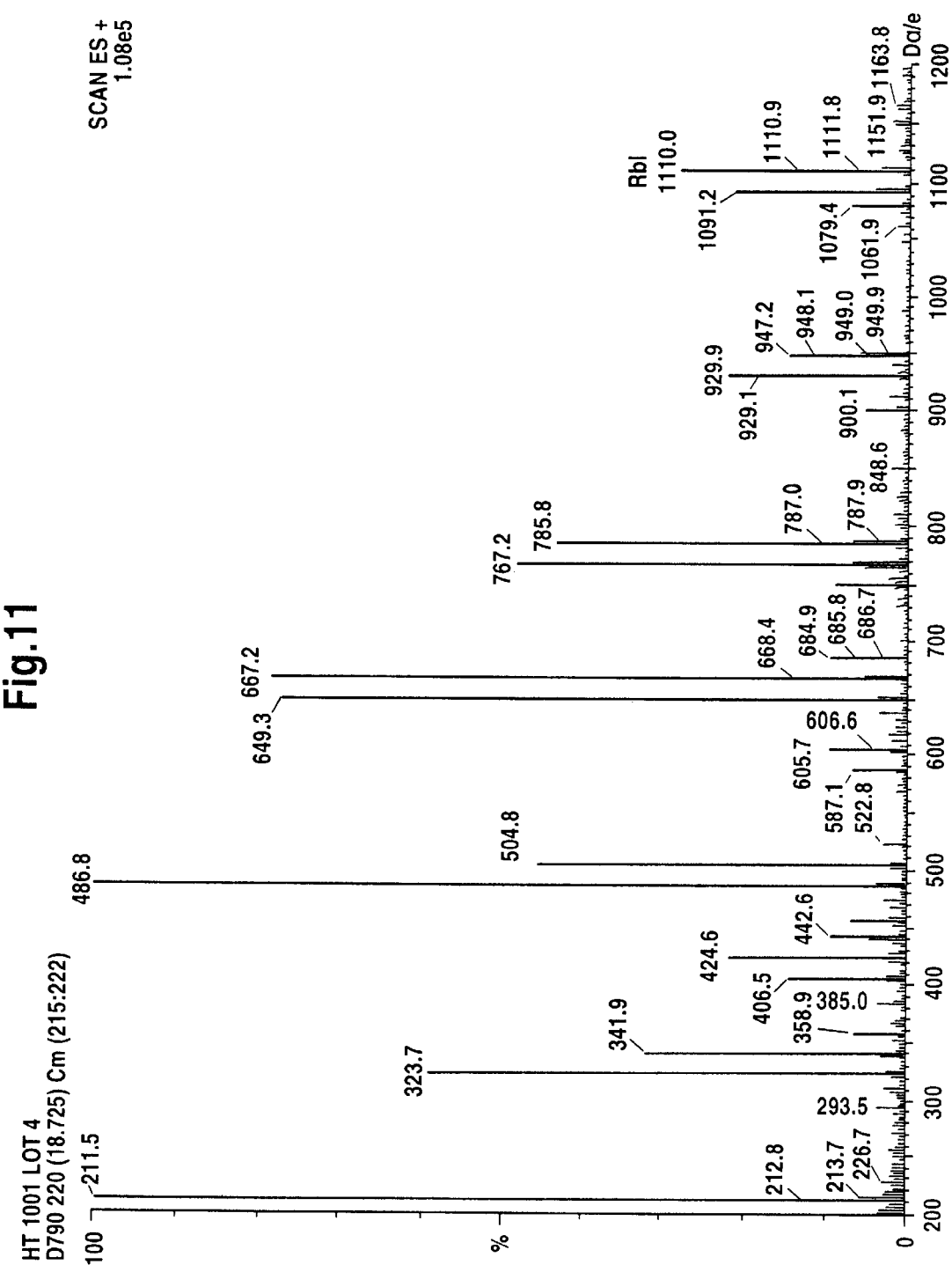
Figure 12:
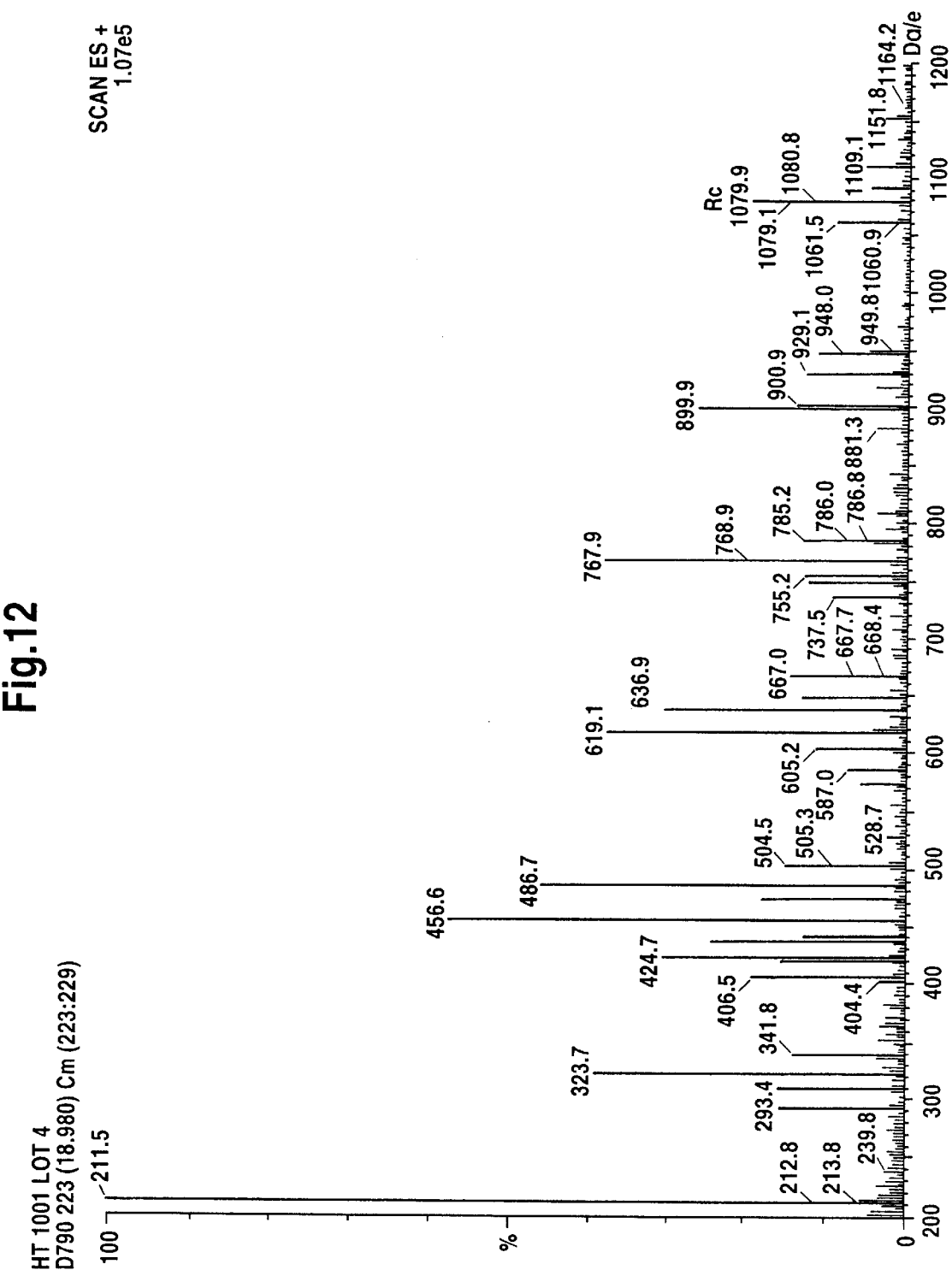
Figure 13:
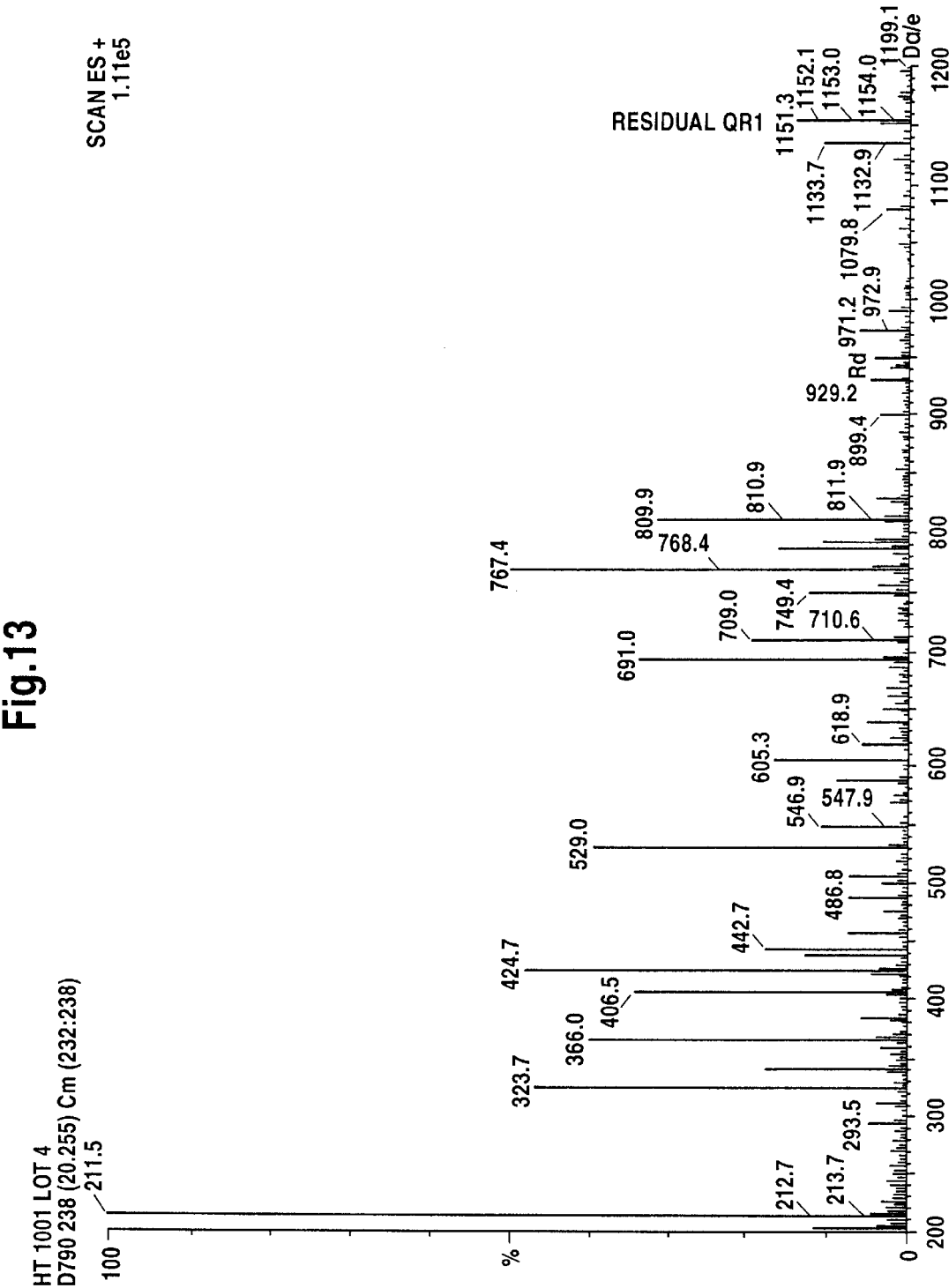
Figure 14:
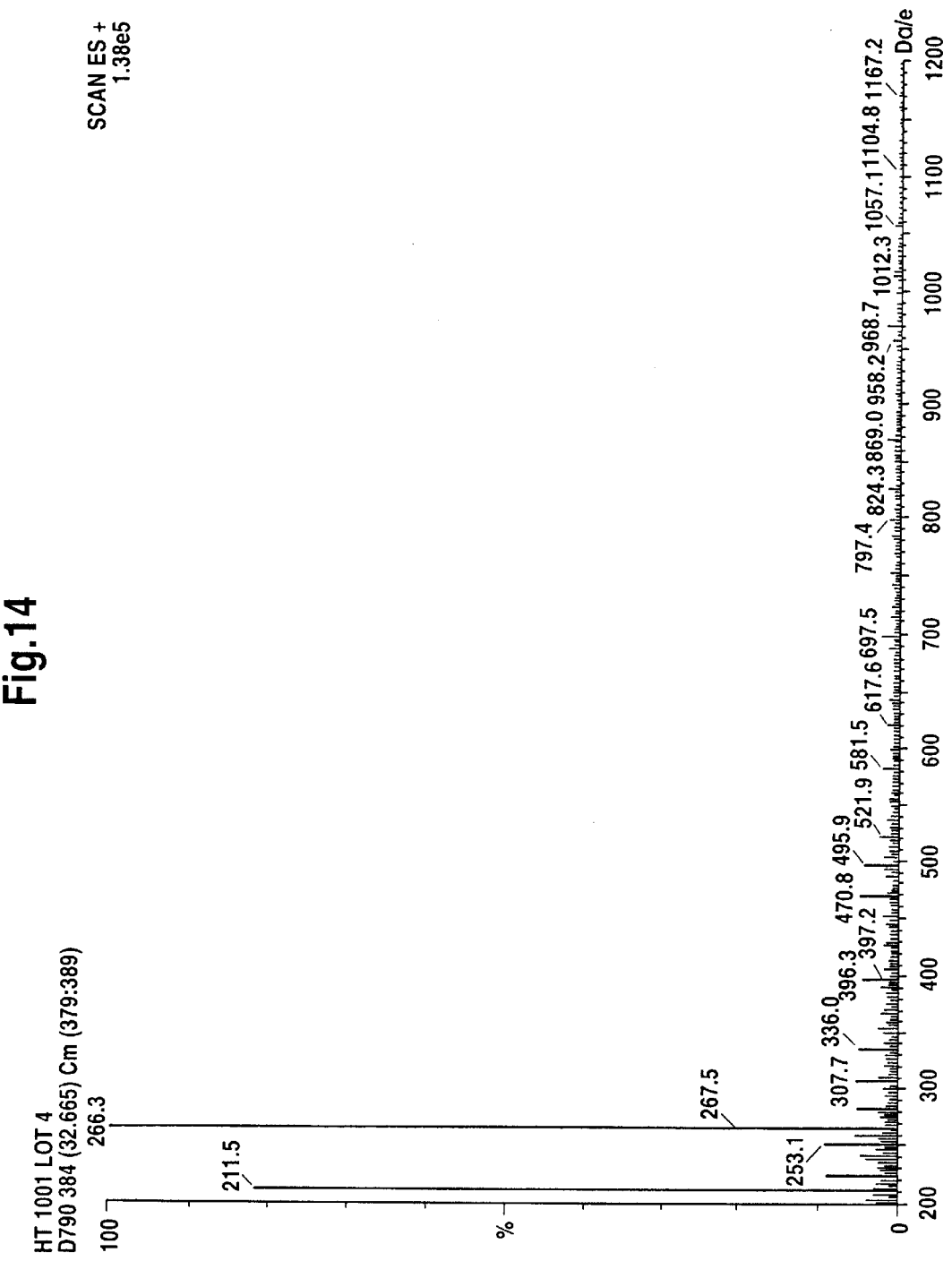

FIGS. 2 and 3 provide ultraviolet absorbance characteristics (uv ANOLOG) and total ion counts (TIC) for lots 3 and 4 respectively. Both lots provide almost identical ultraviolet absorbance chromatograms with the salient features being a distinct peak at 13.7–13.9 minutes, 5 distinct peaks between 17.6 and 19.4 minutes and another distinct peak at 31.7 minutes. Numerous lesser peaks are also distinctive. The seven most prevalent peaks have been designated 1 through 7.

There is an approximately 1 minute delay between recording the ultraviolet signal and the mass spectra signal thus on the total ion count the event at 14.90 minutes corresponds to the ultra violet absorbance event at 13.71 minutes. The following figures illustrate the mass spectra obtained for a number of ion count events and are characteristic of chemicals found in HT1001. Each ion event is identified by numbers in the upper left corner of the spectrum. For example D791 175 (14.900) Cm (170:179) refers to chromatogram run number D791, where the spectrum is centered on scan number 175 at 14.900 minutes and is derived from a combination of scans 170 to 171. Electrospray mass estimates in the molecular weight range of 400–1400 can be expected to have an error of ±one or two mass units.

The following Table summarizes the saponins characteristics of *Panax quinquefolium* and other Panax species.

TABLE 1

| Saponin | Chemical Formula | Molecular Weight |
|---|---|---|
| Rb1 | $C_{54}H_{92}O_{23}$ | 1109.3 |
| Rc | $C_{53}H_{90}O_{22}$ | 1079.3 |
| Rg1 | $C_{42}H_{72}O_{14}$ | 801.0 |
| Rg2 | $C_{42}H_{72}O_{13}$ | 785.0 |
| Re | $C_{48}H_{82}O_{18}$ | 947.2 |
| Rd | $C_{48}H_{82}O_{18}$ | 947.2 |
| Quinquenoside R1 | $C_{56}H_{94}O_{24}$ | 1151.3 |

The following is a list of masses associated with each of the seven prominent peaks and where possible identification of those peaks. FIGS. 4–14 illustrate mass spectra obtained from these peaks in HT-1001 lots 3 and 4.

Peak 1 (FIGS. 4 and 10) is a mixture of two ginsenosides. The first, M+H 801, Fragments 423, 440, 621 was identified as ginsenoside Rg1 MW=800. The second, M+H 948, Fragments 422, 767 was identified as ginsenoside Re MW=947.

Peak 2 (FIGS. 5 and 11) M+H 1110, Fragments 768,486, 501, 667,948. Identified as ginsenoside Rb1 MW=1109.

Peak 3 (FIGS. 6 and 12) M+H 1180, Fragments 899, 456, 637. Identified as ginsenoside Rc MW=1079.

Peak 4 (FIG. 7) Mass unresolved as signal is overshadowed by other components. Possibly ginsenoside Rg2.

Peak 5 (also FIG. 7) M+H 1151, Fragments 810, 423, 528. Identified as quinquenoside R1 (QR1) MW=1151. This is an acetylated form of Rb1 and is found in American Ginseng.

Peak 6 (FIGS. 8 and 13) M+H 948, Fragments 767, 749, 423. Identified as ginsenoside Rd MW=947.

Peak 7 (FIGS. 9 and 14) M+H 266. Identity unknown.

Figure 15:
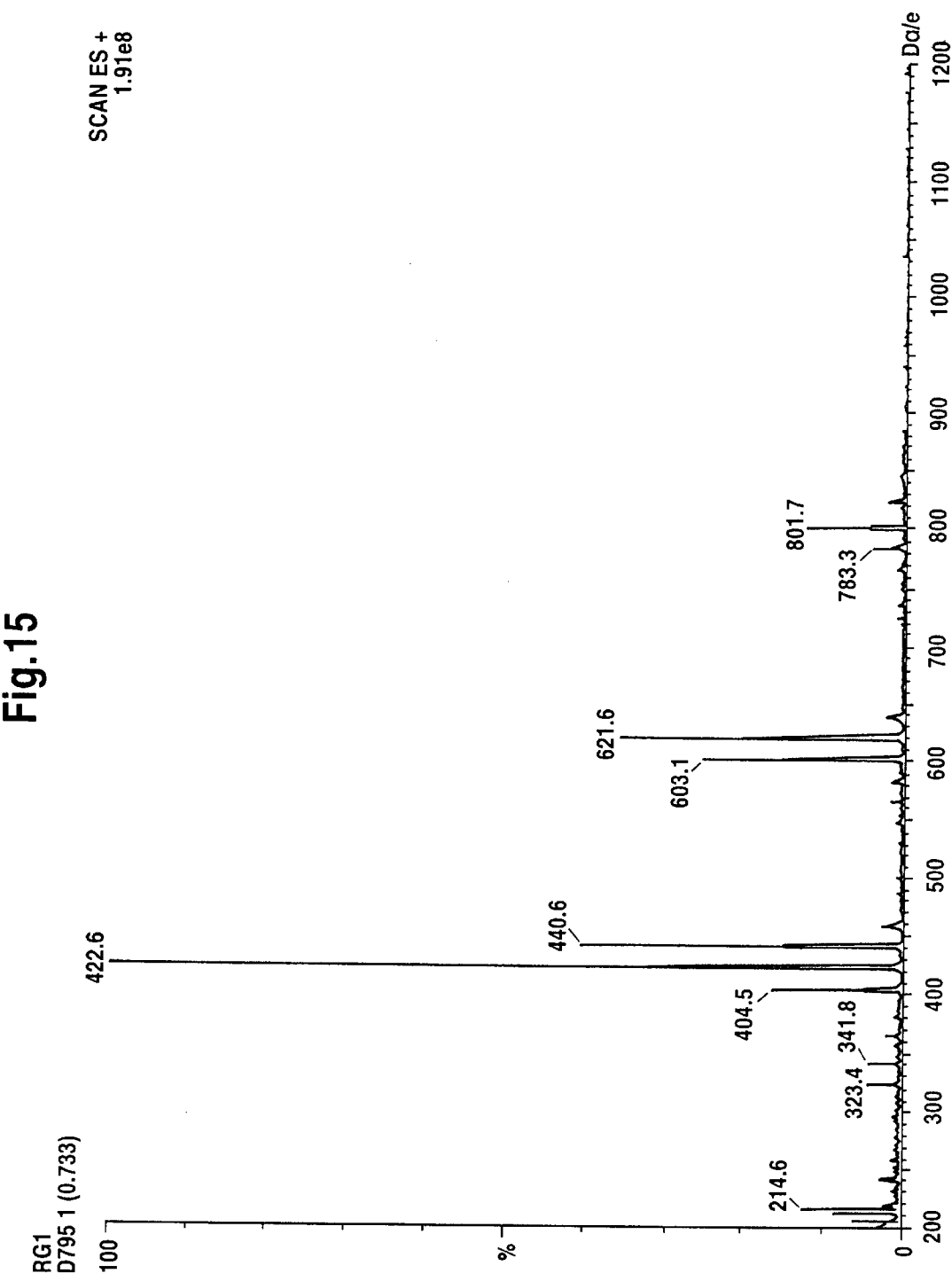
FIGS. 15–20 show mass spectra of pure ginsenosides Rb1, Rg1, Re, Rc, Rd and quinquenoside R1.
Figure 16:
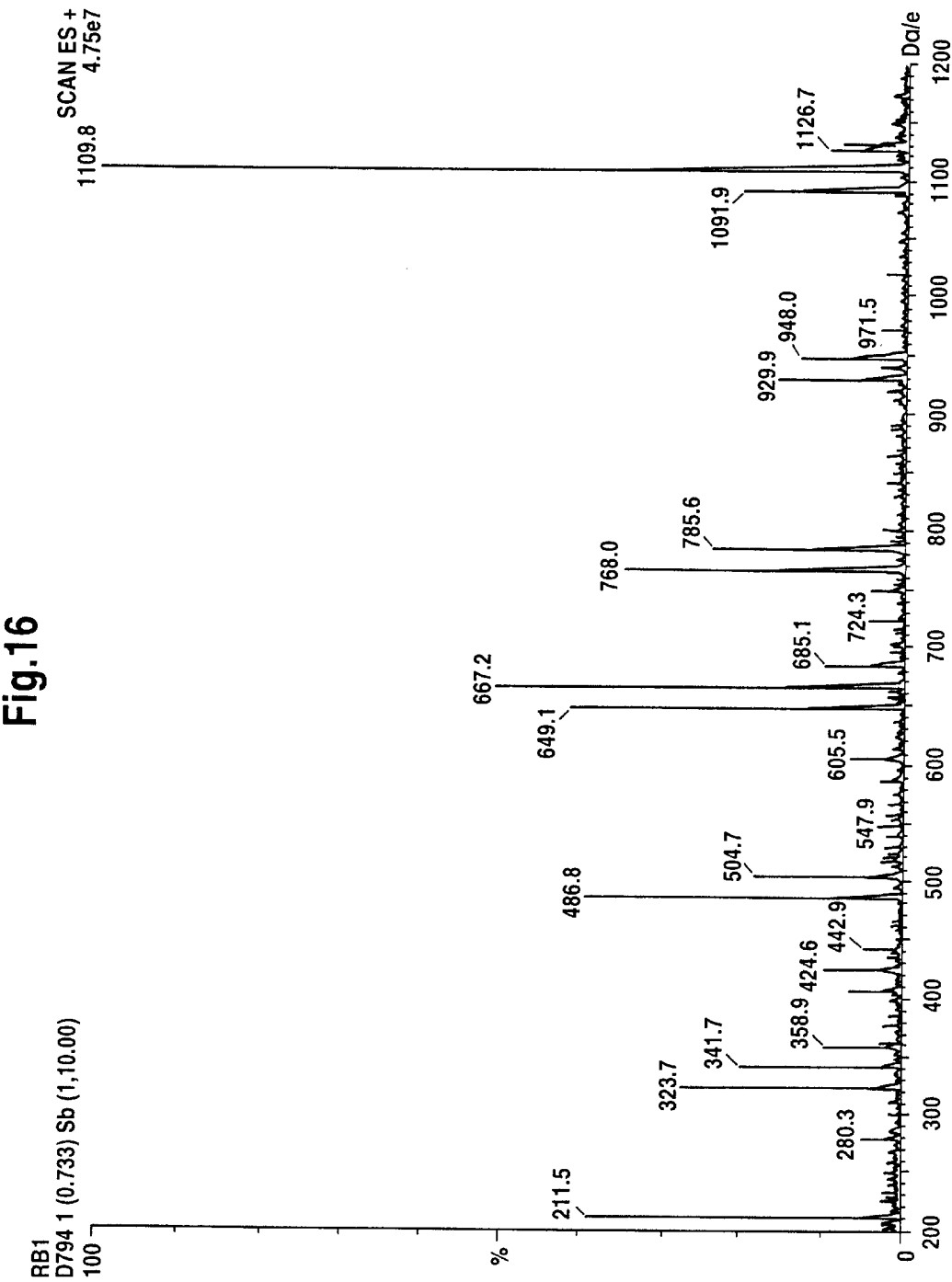
Figure 17:
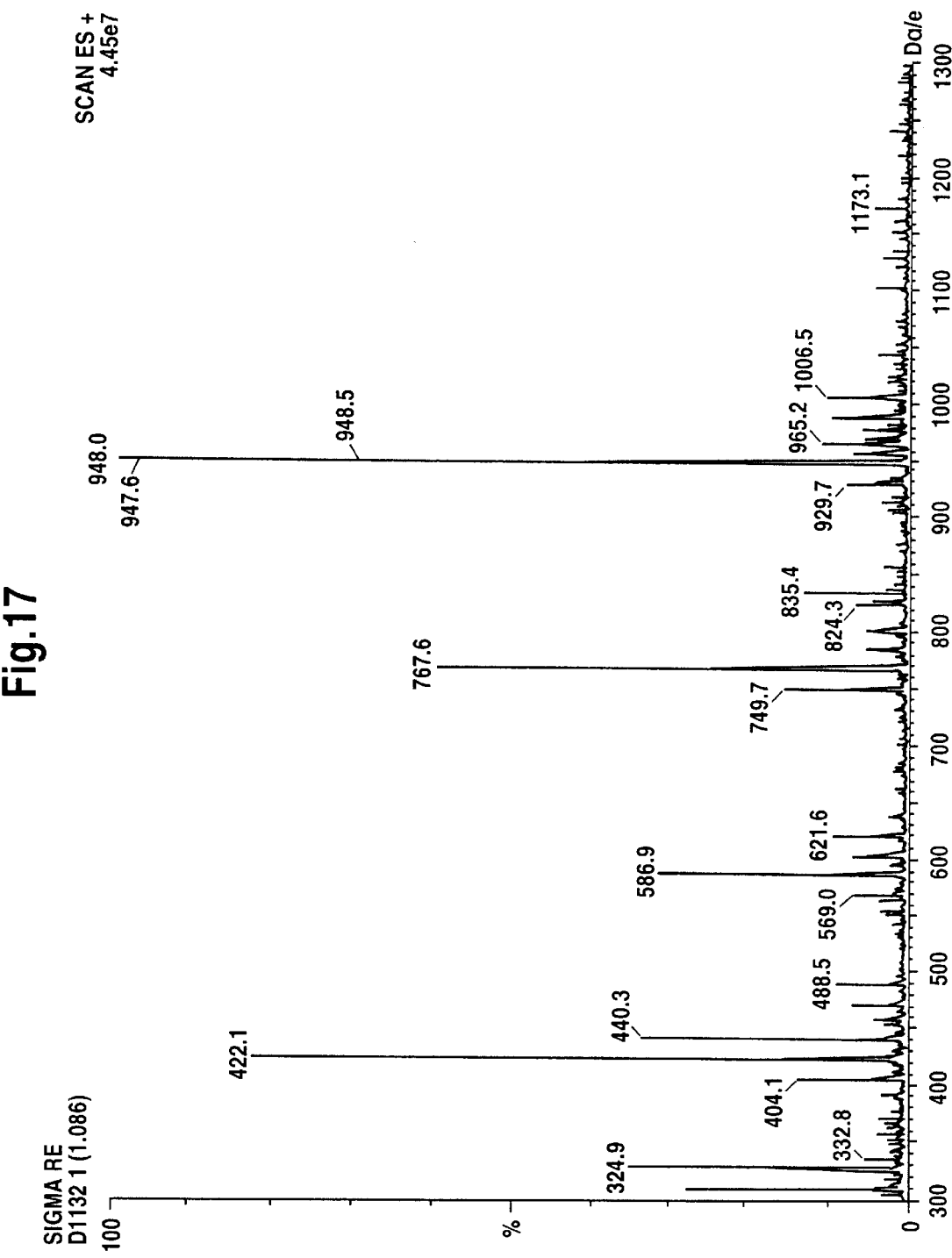
Figure 18:
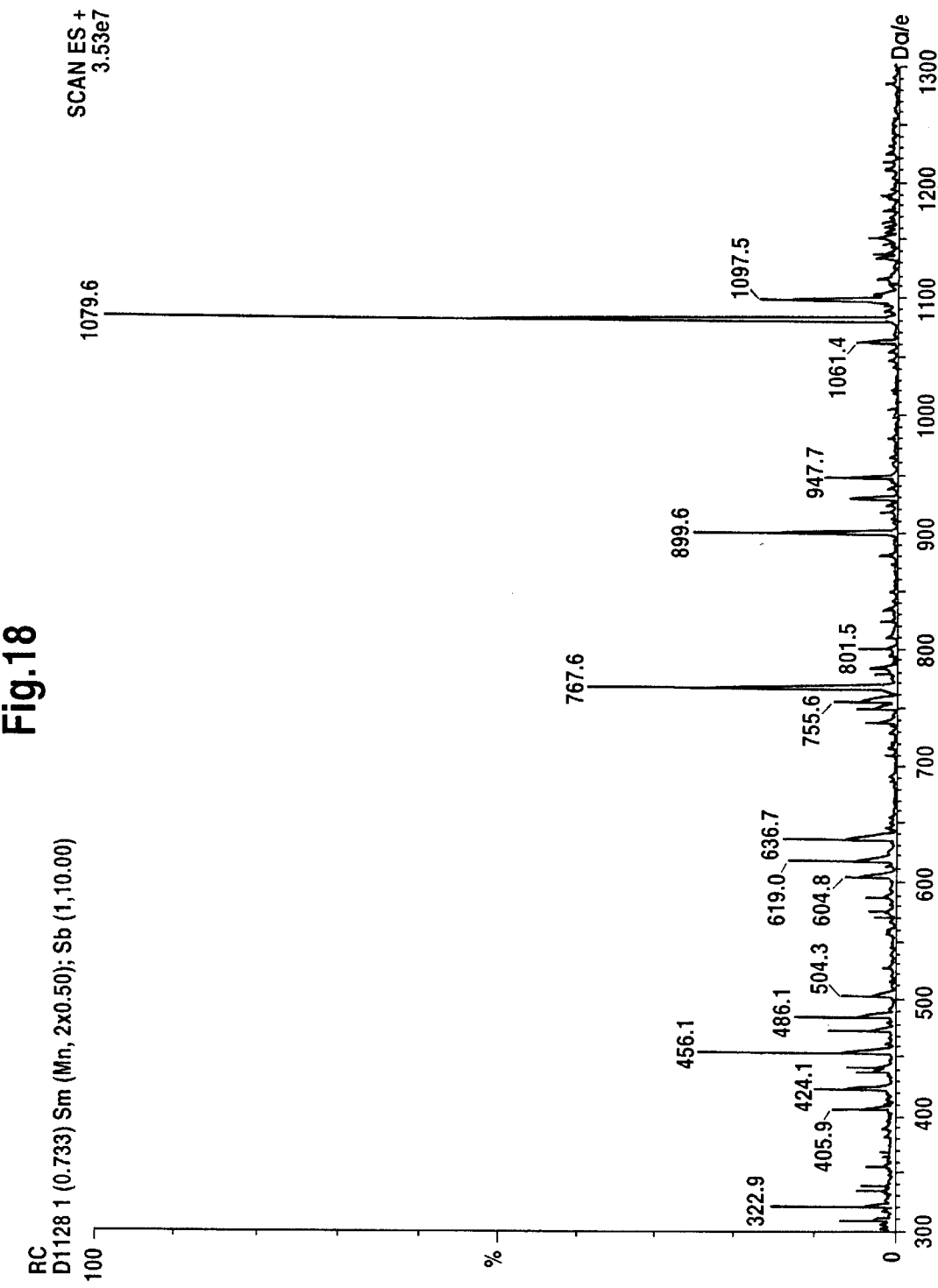
Figure 19:
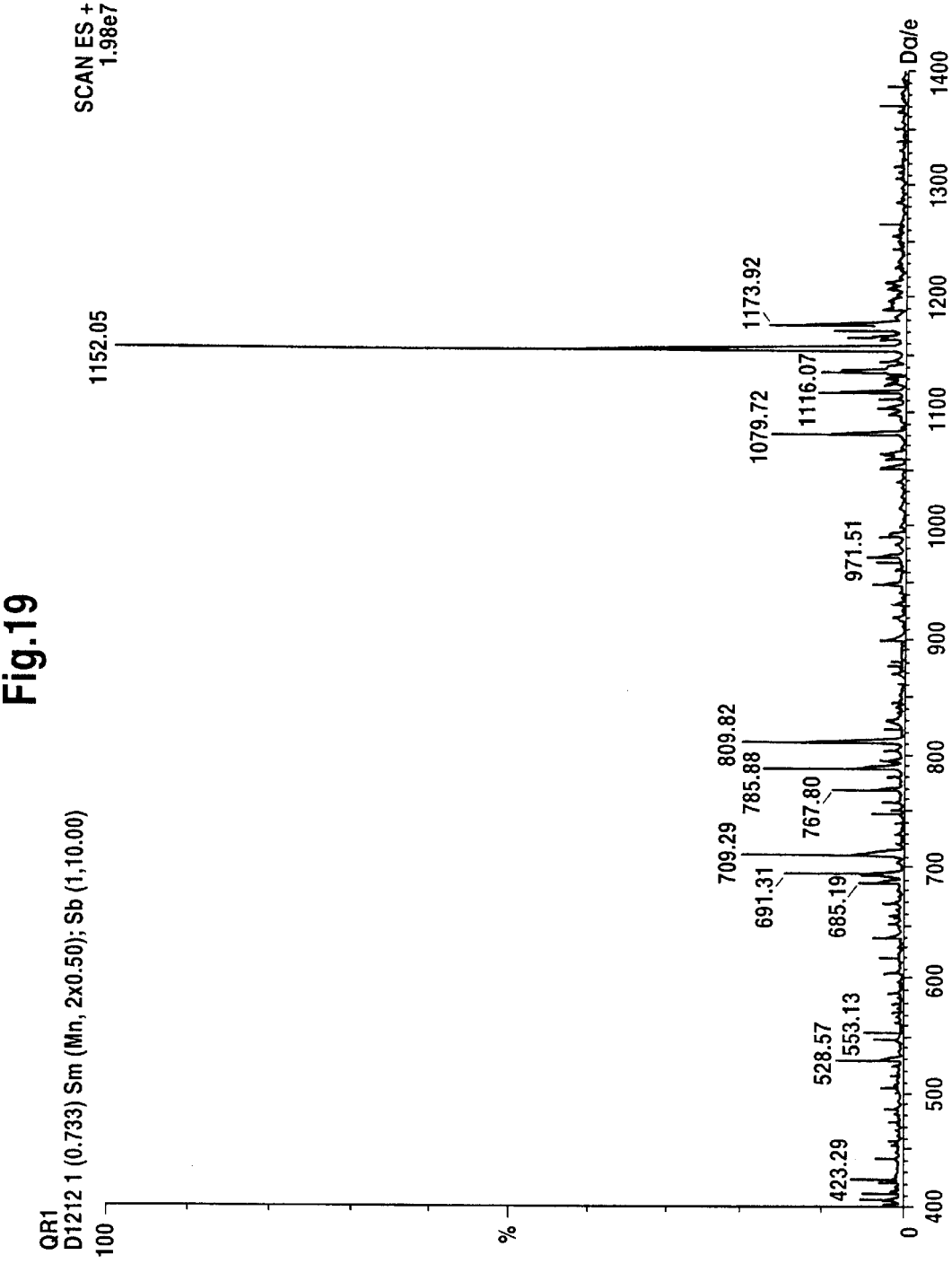
Figure 20:
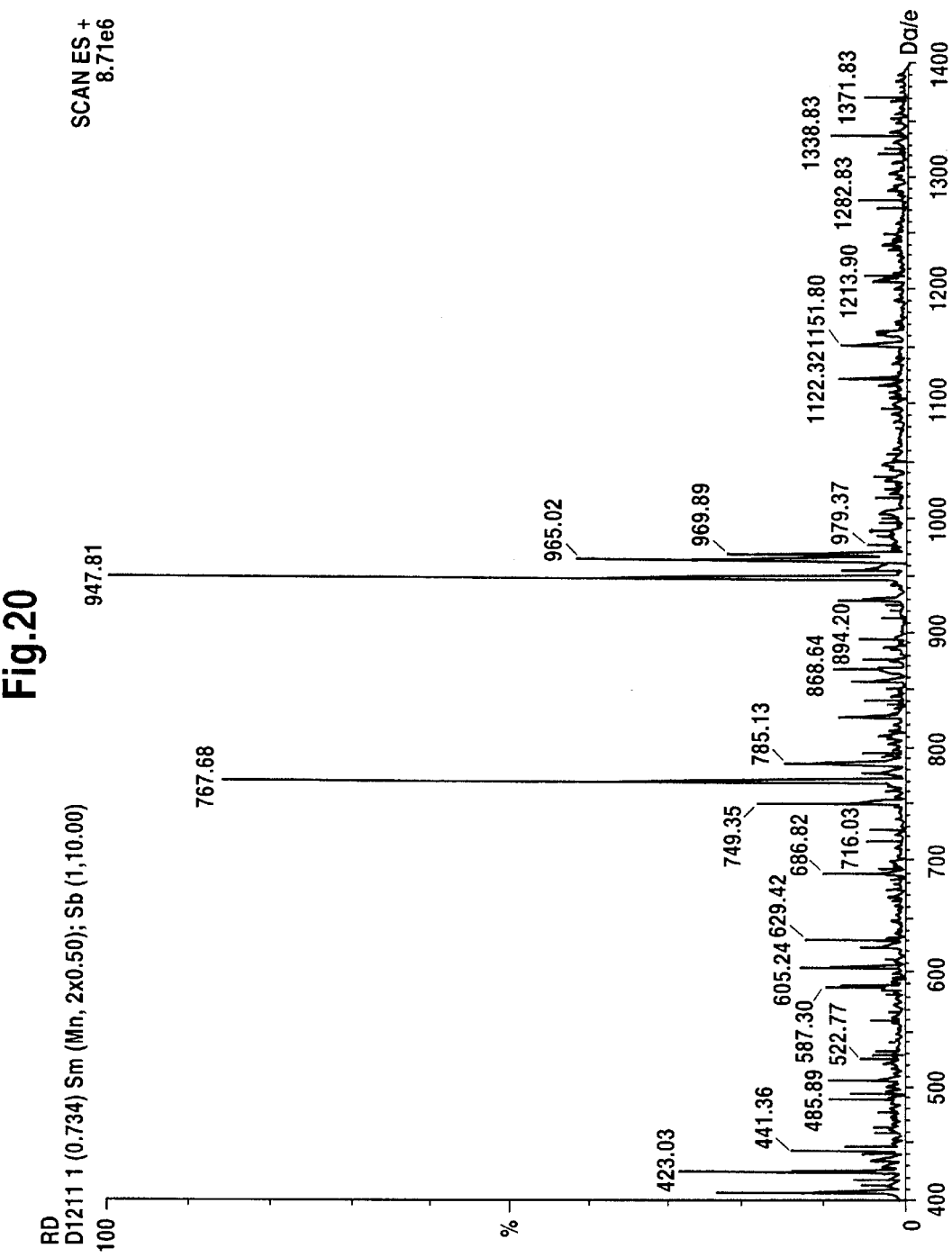

Spectra of pure ginsenosides Rb1 (FIG. 16), Rg1 (FIG. 15), Re (FIG. 17), Rc (FIG. 18), Rd (FIG. 20) and QR1 (FIG. 19) are also provided.

Both lots of HT1001 produce a characteristic ultraviolet absorbance chromatogram when separated in the manner described. Electrospray mass spectrometry provides unequivocal identification of a number of the chemicals separated by the HPLC method and characteristic of HT1001.

Figure 21:
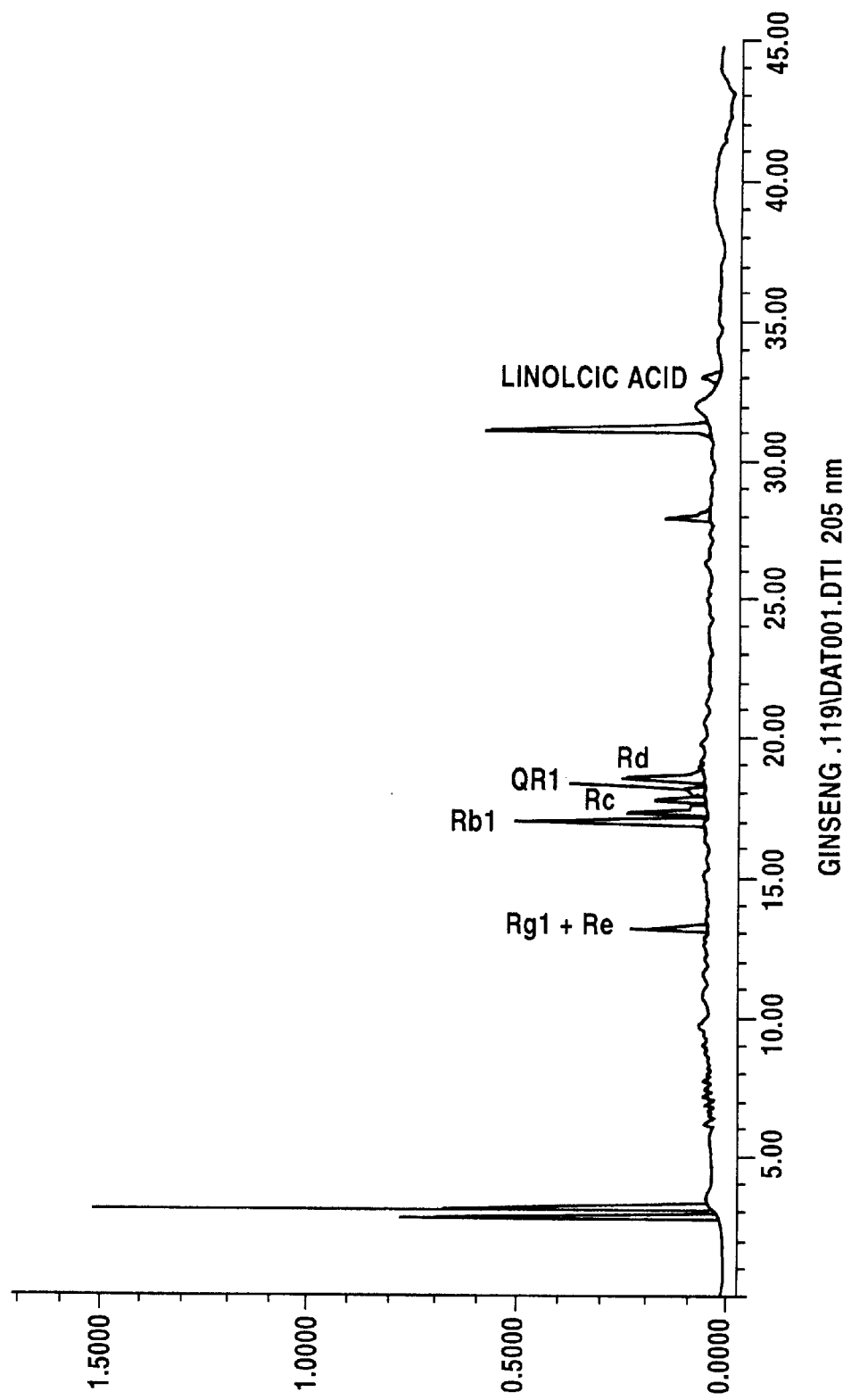
FIGS. 21–24 are chromatograms of HT1001 lot 7, and its fractions PQ4, PQ5 and PQ6.
Figure 22:
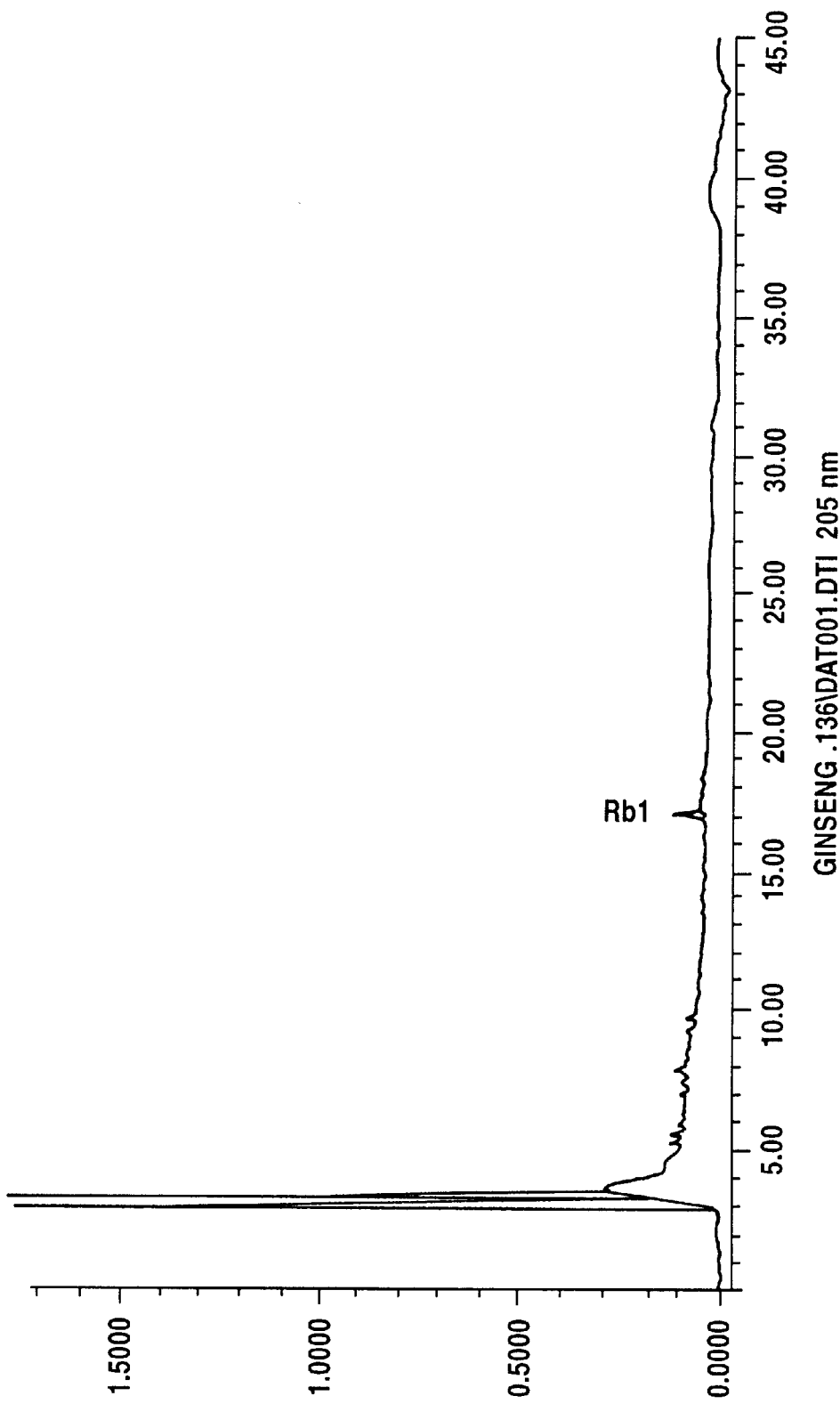
Figure 23:
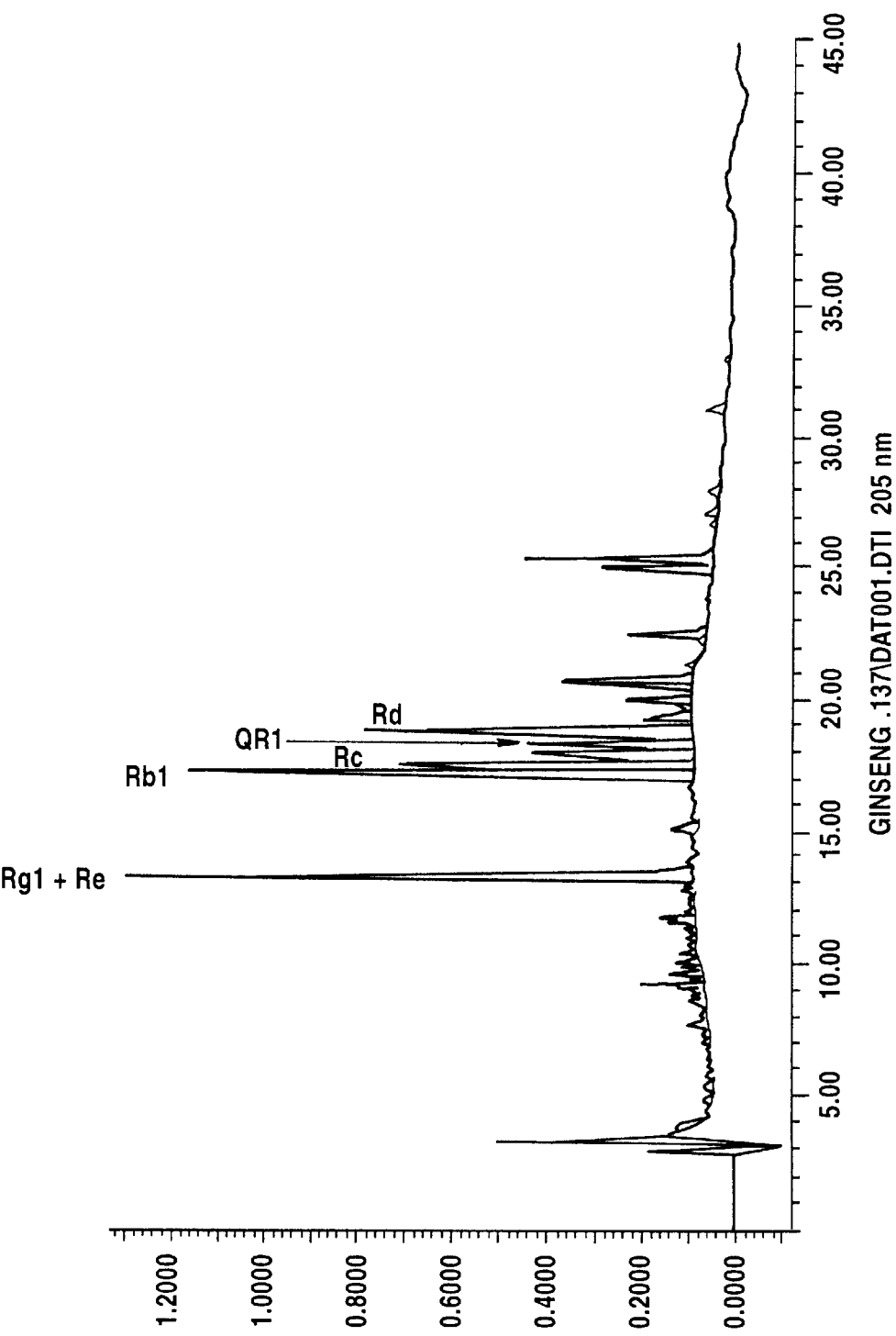
Figure 24:
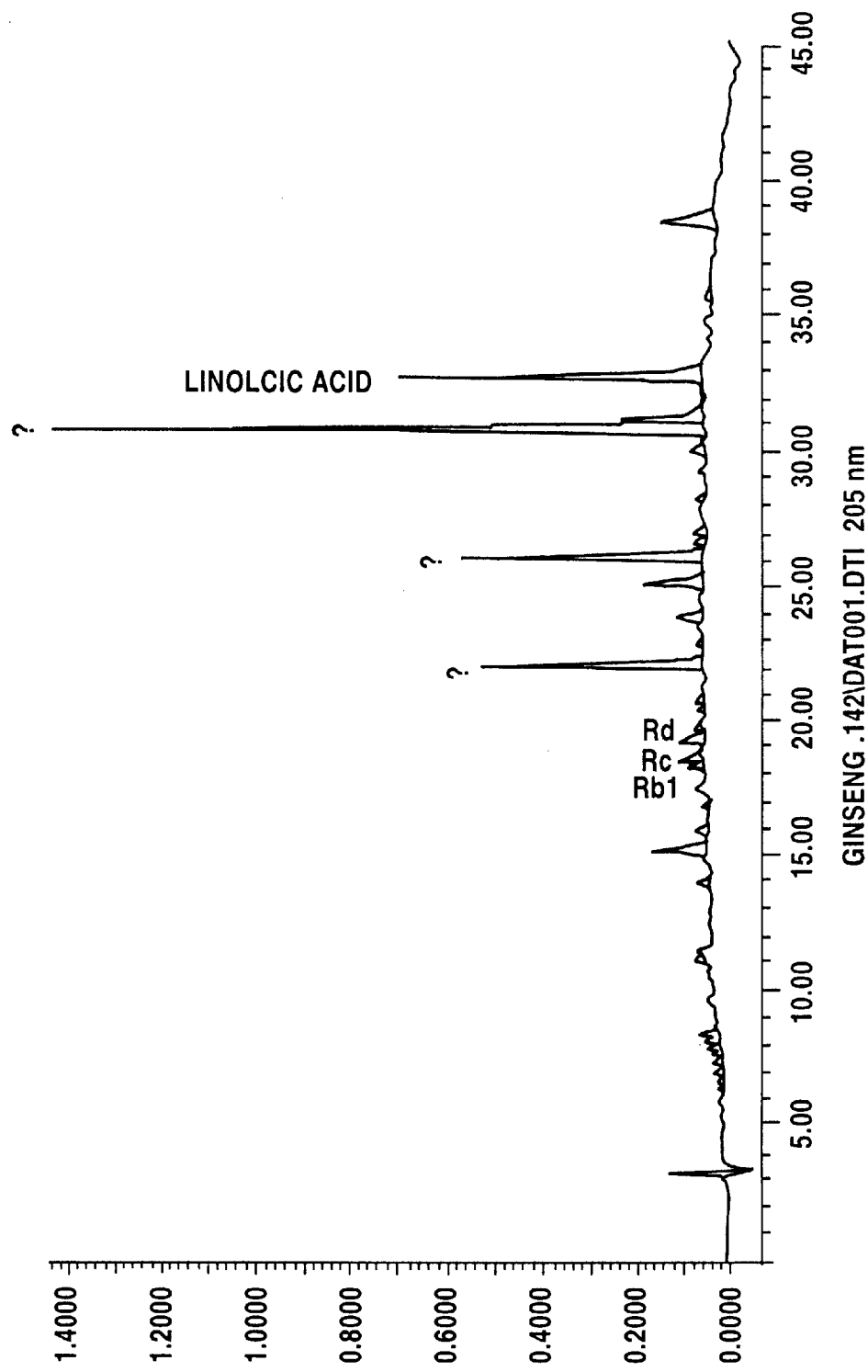

HT-1001 lot #7 was fractionated into 3 fractions designated PQ4, PQ5, and PQ6. Representative chromatograms of HT-1001 lot #7 (FIG. 21) and it fractions (FIGS. 22–24, respectively) are provided.

As is clear from the chemical fingerprinting, HT1001 has the following ultraviolet absorbance characteristics:
a distinct peak between 11 and 16 minutes, more specifically between 13 and 14 minutes;
4–5 distinct peaks between 16 and 23 minutes, more specifically between 17 and 20 minutes; and
a distinct peak between 28 and 35 minutes, more specifically between 31 and 32 minutes.
In addition to these 6–7 most prominent peaks, lesser peaks can also be seen at the following:
2 or more distinct peaks between 2 and 6 minutes;
a distinct peak between 6 and 8 minutes;
a distinct peak between 8 and 11 minutes;
a distinct peak between 11 and 12 minutes;
a distinct peak between 15 and 16 minutes;
2 or more distinct peaks between 23 and 30 minutes, more specifically between 25 and 29 minutes; and
a distinct peak between 31 and 36 minutes.

The present inventors have isolated, identified and, in some cases, tested certain components derived from the major peaks for pharmacological activity. The present inventors believe that certain of the peaks are essential for pharmacological activity. However, the present inventors also believe that certain peaks are non-essential, and not necessary for pharmacological activity, or have little effect on pharmacological activity. For a pharmaceutical composition, it is believed that at least 3 of the 6–7 major peaks in the ultraviolet absorbance figure could be eliminated without significantly affecting pharmacological activity. Thus, only 3–4 of the major peaks in the ultraviolet absorbance figure are required in the pharmaceutical preparation according to the present invention. It is preferred that 4–5 major peaks are included in the pharmaceutical composition, and more preferred if 5–6 of the major peaks are included. It is most preferred if all 6–7 of the major peaks are included.

Of the 9 lesser peaks described above, it is preferred that at least 4 are included in the pharmaceutical preparation according to the invention. It is more preferred if at least 5 are included, and still more preferred if at least 6 are included. It is most preferred that 7 or more are included.

In addition to describing HT1001 by reference to ultraviolet absorbance characteristics, this application also includes figures describing the total ion counts (TIC) for the same two lots of HT1001. As is clear from the figures, HT1001 has the following TIC characteristics:
a distinct peak between 12 and 17 minutes, more specifically between 14 and 16 minutes;
4–5 distinct peaks between 17 and 24 minutes, more specifically between 18 and 21 minutes; and
a distinct peak between 29 and 36 minutes, more specifically between 32 and 33 minutes.
In addition to these 6–7 most prominent peaks, lesser peaks can also be seen at the following:
a distinct peak between 2 and 6 minutes, more specifically between 3 and 5 minutes;
an additional distinct peak between 16 and 19 minutes;
5 or more distinct peaks between 20 and 32 minutes; and
a distinct peak between 33 and 37 minutes.

For a pharmaceutical composition, it is believed that at least 3 of the 6–7 major peaks in the TIC figures could be eliminated without significantly affecting the pharmacological activity. Only 4–5 of the major peaks in the TIC figures are required in the pharmaceutical preparation according to the present invention. It is preferred that 5–6 major peaks are included in the pharmaceutical composition, and more preferred if all 6–7 of the major peaks are included.

Of the 8 lesser peaks described above, it is preferred that at least 4 are included in the pharmaceutical preparation according to the invention. It is more preferred if at least 6 are included, and still more preferred if all 8 are included.

The following concentrations of certain saponins have been determined for HT1001: Rg1+Re: about 3–8%, preferably about 6%; Rb1: about 5–10%, preferably about 8%; Rd: about 1–8%, preferably about 4%; Rc: about 2–8%, preferably about 6%. The total saponin content is between about 20 and 50%, preferably between about 25 and 40%, more preferably between about 30 and 35% and most preferably about 31–33%. Unless otherwise specified, all percentages throughout this description are in terms of weight percent.

HT1001 is preferably further extracted to give 3 portions, a total oligosaccharides portion (PQ4), a total saponins portion (PQ5) and a total essential oil portion (PQ6). The resulting proportions for each fraction, compared to the entire HT1001 extract, are about 40–60%, preferably about 48%, about 20–50%, preferably about 40%, and about 4–9%, preferably about 6%, respectively. A discription of the process used to produce HT1001 fractions PQ4, PQ5 and PQ6 is attached as FIG. 25.

A sample of 1 mg of total saponins (PQ5) was analyzed by HPLC electrospray mass spectrometry as previously described. The saponins Rg1, Re, Rb1, Rc, quinquenoside R1 (QR1) and Rd were evident. See FIG. 23. The solvent front was much reduced and the late peak corresponding to mass 265 was almost absent when compared to HT1001. As indicated in the chemical fingerprint shown in FIGS. 2 and 3, HT1001 contains mainly substances eluting between 5 and 28 minutes with 5–6 distinct peaks between 11 and 25 minutes in HPLC-UV absorbance.

A small sample (100 μg) of essential oil (PQ6) was dissolved in 50% acetonitrile and chromatographed as previously described. When compared to HT1001, the solvent front and saponins are almost completely absent. See FIG. 24. Two major UV absorbing peaks are the major components. This portion contains mainly substances eluting between 22 and 37 minutes with one distinct peak between 29 and 33 minutes and a second peak (linoleic acid) between 33 and 36 minutes in HPLC-UV absorbence. Two lesser peaks are now evident.

A small sample of total oligosaccharides (PQ4) was dissolved in water and chromatographed by HPLC electrospray mass spectrometry as previously described. When compared to HT1001, only the solvent-front between 2 and 5 minutes is evident. See FIG. 22. This portion is characterized as saccharides and oligosaccharides using cellulose-paper chromatography. HT1001 contains approximately 40–60% PQ4. PQ4 consists of 10–15% glucose, 60–65% disaccharides, 3–5% trisaccharides and 10–15% polysaccharides.

HT1001 is useful as treatment for a variety of brain conditions or illnesses and for general cognitive improvement. Suitable brain conditions to be treated include senile dementia, Alzheimer's disease, Parkinson's disease, attention deficit disorder, mental retardation and stroke. HT1001 is also useful for treating depression.

HT1001 may also be used to improve learning ability or memory.

Preferable administration of HT1001 is oral, but it is also possible to apply HT1001 intravenously. Suitable carriers, diluents or excipients are known in the art for preparing pharmaceutical compositions. Such suitable diluents or excipients include, but are not limited to, water, salt solutions, alcohols, gum arabic, vegetable oils, polyethylene glycols, gelatine, lactose, amylose, magnesium stearate, talc, starches such as corn or potato starches, silicic acid, viscous paraffin, fatty acid monoglycerides and diglycerides, pentaerythritol fatty acid esters, hydroxymethylcellulose, polyvinyl pyrrolidone, etc. The pharmaceutical composition can be sterilized and, if desired, mixed with auxiliary agents, such as lubricants, preservatives, stabilizers, wetting agents, emulsifiers, salts for influencing osmotic pressure, buffers, coloring, flavoring and/or aromatic substances. It is preferred that administration of HT1001, or a pharmaceutical composition containing HT1001 with or without elimination of any non-essential peaks as referred to above, is made in a dosage range of 10–1000 mg of active agent for a 75 kg individual per day. It is more preferred to use a dosage of 75–500 mg per individual per day, and most preferred to use a dosage of 100–200 mg per individual per day.

The phrase "effective amount" as used herein includes the administration of HT1001 alone, or in combination with a known effective ingredient. The normally-effective amount of HT1001 can be reduced if the HT1001 is co-administered with a natural or synthetic compound which is known to be effective in treating brain conditions, such as *Gingko biloba* or Deprenyl. Thus, the term "effective amount" is intended to cover the use of HT1001 in combination with a known effective ingredient, whereby the combination of the ingredients is effective, and the dosage of each ingredient can be proportionally reduced. For example, if HT1001 is normally administered effectively at 100 mg per individual per day, and *Gingko biloba* is normally administered effectively at 100 mg per individual per day, a combination of the two ingredients may be used whereby each is administered at 50 mg per individual per day. Such a combination use can be cost effective for the consumer if the other active ingredient (besides HT1001) is expensive, as is the case with many pharmaceuticals.

Studies have been conducted on the pharmacological effects of HT1001. The studies are presented as the following Examples.

EXAMPLE 1

Example 1 is a study of the effects of several extracts of HT1001, PQ4, PQ5, PQ6 and pure ginsenosides, on monoamine oxidase A (MAO A) and monoamine oxidase B (MAO B) activity in vitro.

HT-1001, related extracts and pure ginsenosides were evaluated for in vitro monoamine oxidase-A and monoamine oxidase-B inhibiting activity using the radiochemical procedure of Lyles and Callingham, *Biochem. Pharmacol.* 31: 1417–1424 (1982), employing either radiolabelled 5-hydroxytryptamine or β-phenylethylamine as substrates for monoamine oxidase-A (MAO-A) or monoamine oxidase-B (MAO-B) respectively. Various concentrations of the compounds of interest were incubated in appropriately diluted homogenates of rat brain in a 0.2 M potassium phosphate buffer. After a 15 minute preincubation period the reaction was initiated by the addition of substrate. Incubations proceded at 37° C. for 10 minutes. Incubation was terminated by the addition of acid and the radiolabelled products (5-hydroxyindoleacetic acid, 5-hydroxyindoleacetaldehyde or phenylacetic acid, phenylacetaldehyde) were extracted and quantified by liquid scintillation counting procedures. Incubations were done in triplicate and incubations including pheneizine a known MAO inhibitor were included as controls and for comparison. The percent inhibition of monoamine oxidase-A or monoamine oxidase-B activity compared to controls containing no experimental material was calculated.

A significant amount of MAO inhibiting activity was produced by HT-1001 lots 3 and 4 at a concentration of 10 mg/ml (Table 2). Further evaluation of HT-1001 the derived products PQ4, PQ5, PQ6 and pure ginsenosides demonstrated that most of the MAO inhibiting activity resided in the PQ6 fraction. PQ6 was further fractionated into a saponin containing fraction (PQ6-S) and a lipid containing fraction (PQ6-L). Both PQ6-S and PQ6-L had comparable MAO inhibiting properties to each other and to the original PQ6 material.

TABLE 2

| Material | Dose | % MAO-A Inhibition | % MAO-B Inhibition |
|---|---|---|---|
| HT1001 (Lot #3) | 1.0 mg/ml | 16.9 | 18.4 |
| | 10 mg/ml | 66.9 | 40.2 |
| HT1001 (Lot #4) | 1.0 mg/ml | 14.1 | 22.3 |
| | 10 mg/ml | 68.2 | 46.2 |
| PQ4 | 0.10 mg/ml | −9.5 | −0.9 |
| | 1.0 mg/ml | −1.4 | −6.7 |
| | 10 mg/ml | 21.5 | 12.3 |
| PQ5 | 0.10 mg/ml | −10.1 | −14.1 |
| | 1.0 mg/ml | −15.3 | −15.9 |
| | 10 mg/ml | 15.4 | 19.7 |
| PQ6 | 0.10 mg/ml | 21.3 | 22.3 |
| | 1.0 mg/ml | 36.9 | 39.2 |
| | 10 mg/ml | 79.0 | 86.0 |
| PQ6-S | 0.10 mg/ml | 11.4 | 9.8 |
| | 1.0 mg/ml | 40.2 | 34.4 |
| | 10 mg/ml | 72.5 | 69.4 |
| PQ6-L | 0.10 mg/ml | 10.1 | 15.0 |
| | 1.0 mg/ml | 36.4 | 39.0 |
| | 10 mg/ml | 63.3 | 76.1 |
| Rb1 | 1.0 mg/ml | −6.9 | −11.6 |
| | 10 mg/ml | 7.1 | −7.8 |
| Rg1 | 1.0 mg/ml | −10.8 | −7.2 |
| | 10 mg/ml | 5.1 | −5.0 |

Values are based on one assay performed in triplicate

EXAMPLE 2

Example 2 is a comparison of several batches of Rb1 extract, an extract of total ginsenosides (TS) containing 25% Rb1, 19.4% Rc1 and 21.6% Rg1+Re, and HT1001 on choline uptake in rat brain synaptomes. The Rb1 tested had greater than 98% purity. Rb1-52, Rb1-53 and Rb1-54 represent three different batches of Rb1. As the following table makes clear, HT1001 significantly increases choline uptake at concentrations of 0.9 and 9 mg/l.

TABLE 3

| Extract | Values per Concentration (mg/l) (expressed as % of control) | | | | |
|---|---|---|---|---|---|
| Concentration | 0.0011 | 0.011 | 0.11 | 1.1 | 11 |
| Rb1-52 | 108 ± 5.7 | 108 ± 4.4 | 108 ± 5.8 | 109 ± 5.4* | 111 ± 3.7* |
| Rb1-53 | 106 ± 1.3 | 109 ± 3.6 | 109 ± 3.8 | 112 ± 4.8* | 114 ± 2.5** |
| Rb1-54 | 108 ± 3 | 110 ± 3.4 | 110 ± 2.6 | 112 ± 1.2* | 111 ± 2.6** |
| Concentration | 0.0009 | 0.009 | 0.09 | 0.9 | 9 |
| TS | 101 ± 1.7 | 104 ± 2.8 | 104 ± 3.2 | 106 ± 4.6 | 115 ± 5.9* |
| HT1001 | 106 ± 2.6 | 109 ± 5.8 | 113 ± 3.7 | 121 ± 1** | 124 ± 2.6** |

Values represent mean ±SE. n = 4. *P < 0.05, **P < 0.01 student T test, compared to control.

EXAMPLE 3

Several tests were conducted on the effects of HT1001 on learning and memory, choline uptake in synaptosomes prepared from rat hippocampus, the immunostimulatory effects of HT1001, the effects of HT1001 on aminergic neurotransmitters and antimicrobial effects of HT1001.

In order to show that HT1001 is a more efficacious product than crude ginseng we wanted to demonstrate that after oral administration, HT1001 provides greater blood concentrations of particular ginsenosides than crude ginseng containing equivalent amounts of ginsenosides. We provided rats with oral doses of either 100 mg/kg HT1001 (8 mg/kg Rb1) or crude ginseng powder 500 mg/kg (8 mg/kg Rb1). Higher doses of HT1001 are unreasonable as we cannot feed the rats an equivalent concentration of Rb1 in ginseng powder. After one hour blood samples were taken and we attempted to measure the Rb1, concentration in the serum. Samples with higher Rb1 concentrations would indicate greater bioavailability. Unfortunately, the concentrations of Rb1, in the serum after oral administration of 100 mg/kg HT1001 or 500 mg/kg ginseng powder are too low to measure using our present techniques.

TABLE 4

Serum Concentrations of Rb1 in Rats Following Feeding with Water, Ginseng Powder or HT1001.

| Treatment | Amount Rb1 Administered (mg/kg) | Serum Rb1, Concentrations ($\mu$g/ml) |
| --- | --- | --- |
| Water (1 ml) | 0 | Not Detected |
| Ginseng Powder (500 mg/kg, 1 hour) | 8 | Not Detected |
| HT1001 (100 mg/kg, 1 hour) | 8 | Not Detected |
| HT1001 (1000 mg/kg, 1 hour) | 80 | 2.45 ± 0.60 |

Values are the mean ± the standard error based on 5 determinations. The limit of detection is 0.5 $\mu$g/ml.

First, we studied the effects of HT1001 on Learning and Memory. Ginsenosides including Rb1, have been demonstrated to enhance learning and memory. As HT1001 is a mixture of ginsenosides, it may not have the same properties as pure Rb1. In order to show that HT1001 can enhance learning and memory we wanted to demonstrate that this product can provide a measurable increase in task acquisition and/or retention in a scientifically accepted learning paradigm. The Morris water maze is a scientifically demonstrated procedure which can test spatial learning and memory. Rats are required to learn the location of a hidden platform in a swimming pool. If rats treated with HT1001 learn the location of the platform faster than rats not treated with HT1001 then it is demonstrated that HT1001 enhances learning. The effects of HT1001 on memory can also be examined in scopolamine induced amnesia. If HT1001 enhances memory it should protect against memory loss in scopolamine treated animals.

The methodology and experimental design for our study is, as follows.

Morris Water Maze Task

The Morris water maze task was based on methods previously described (Pitsikas et al, *Pharmacol. Biochem. Behav.* 47: 95–99 (1994); Smith et al, *Psychopharmacol.* 114: 651–656 (1994)). The apparatatus consisted of a circular pool (1.7 m diameter, 35 cm deep) which contained water (30° C.) made cloudy by the presence of powdered milk. A moveable platform (10 cm×11.5 cm and 20 cm tall) was placed in the pool such that it was submerged by 3 cm and could not be seen. Each trial involved placing the rat in the pool in one of the four equally spaced quadrants in which the pool was divided. Visual cues consisting of large posters were placed on the walls of the room in which the experiment was conducted, and the experimenters maintained established positions throughout each experiment. During the learning period, animals were allowed to swim freely until they found the escape platform. If a rat failed to find the platform within the allotted period (300 seconds, initial learning period; 180 seconds, scopolamine-induced amnesia trials), it was placed on the platform by the experimenter for 30 seconds. During the initial learning period, all rats were tested sequentially and were given 4 trials per day during which the escape platform was located in a fixed position in the center of the pool. During the scopolamine trials rats were tested sequentially three times on each day with the three trials being performed between 30 and 45 minutes following scopolamine or saline injection, The latency to reach the platform was recorded.

Experimental Design for Learning and Memory Testing

The specific aim of the experiment was to test if HT1001 affected the acquisition, retention and/or recall of a new task in the presence of scopolamine-induced amnesia. Rats were initially divided into two groups and fed either water (0.5 ml) or HT1001 (200 mg/kg/day in 0.5 ml water by gavage) for the duration of the experiment. Eight days after the initiation of water or HT1001 administration, rats were given the task of learning the position of a platform concealed at the center of the Morris water maze. The rats were placed in the pool 4 times per day for 5 days and the time required to find the platform was recorded (maximum duration 300 seconds). Latency became shorter as the rats learned the task. On day 14, the two groups of rats were further subdivided into four groups. Six rats from each of the initial two groups received saline injections while the remaining six rats from each initial group received scopolamine (2 mg/kg) prior to being required to find the platform which had been moved to the center of quadrant 1 (3 trials, maximum duration 180 seconds between 30 and 45 minutes of receiving either saline or scopolamine injection). On day 15, the procedure for day 14 was repeated with the platform remaining located in the position designated on day 14. On day 16, the procedure from day 14 was again followed except that the platform was moved to a new location on the opposite side of the pool (center of quadrant 3). On day 17, the procedure followed on day 16 was repeated. In each instance the time to locate the platform (latency) was recorded.

This entire experiment was repeated twice using 24 rats each time. The data from the two experiments was combined. One HT1001-treated rat died ftom accidental administration of HT1001 into the lungs. One control rat failed to find the platform on the last five trials of the learning curve. This data has been eliminated although it does not significantly affect the results. One HT1001 fed and scopolamine injected rat failed to find the platform on the final day and was excluded.

We have completed several studies on spacial learning and memory using the Morris water maze and scopolamine induced amnesia with HT1001 as the test compound. The combined results of the final two experiments follow.

Escape Latencies

Figure 26:
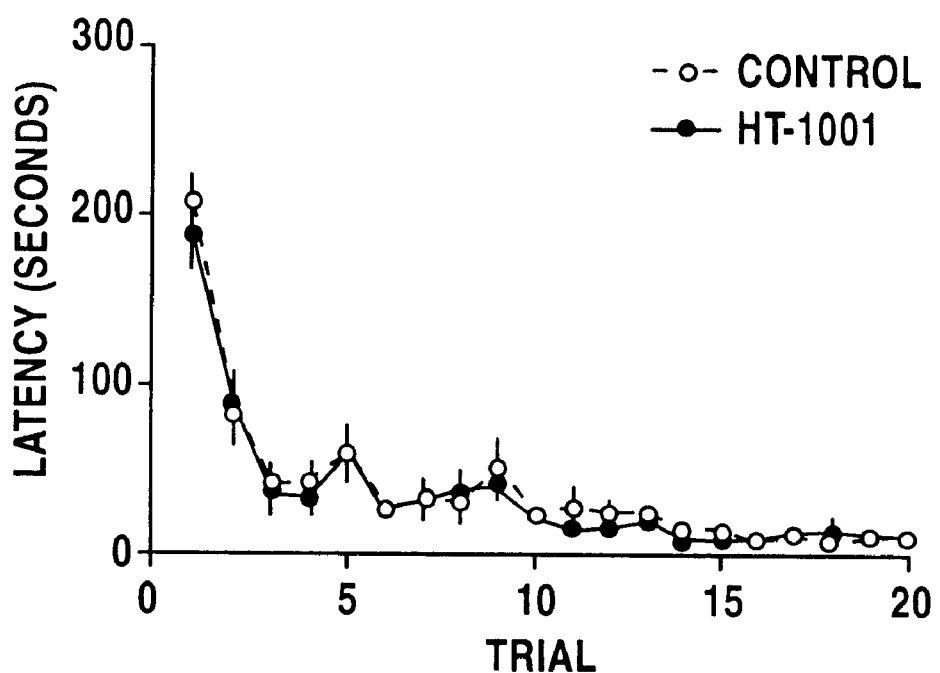
FIG. 26 shows the escape latencies of rats in the Morris water maze before testing.

Rats rapidly learned the location of the escape platform in the Morris water maze (FIG. 26). In both replications, animals reached asymptotic performance on day three of testing. The presence of HT1001 in the diet had no effect on the initial learning task.

Figure 27A:
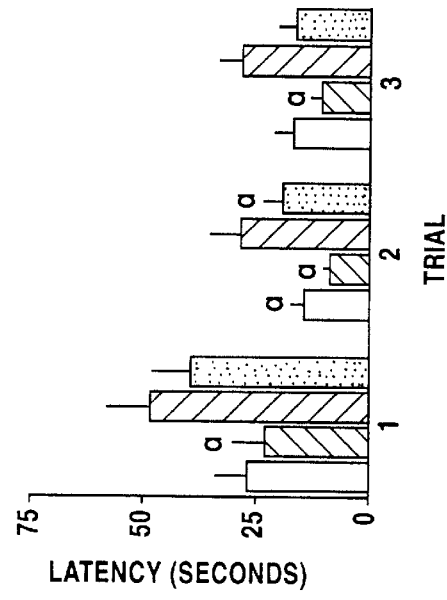
FIGS. 27A–D show test results from rats treated with HT1001 in the Morris water maze.

When rats were required to initially learn a new location for the platform following initial training (day 14) a significant effect was determined only in the third trial where saline treated animals (mean latency 17.2±2.8 (23) seconds) outperformed scopolamine treated animals (mean latency (39.5±8.2 (24) seconds) p<0.05. In particular, HT1001/saline treated animals outperformed control/scopolamine treated (FIG. 27a).

Figure 27B:
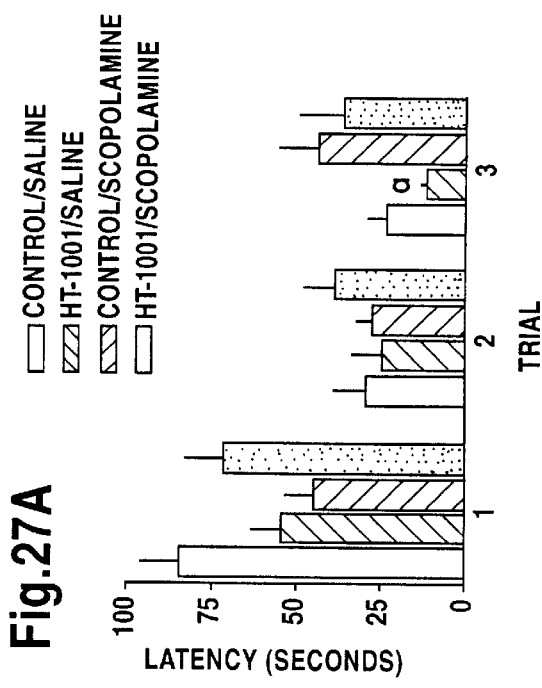

When the rats were required to remember the new location of the platform on the following day (day 15) HT1001/saline treated animals significantly outperformed control/scopolamine treated rats in each trial (FIG. 27b), Furthermore, in the second trial control/scopolamine treated rats took significantly longer than each of the other treatment groups to find the platform (FIG. 27b). When the data from the three consecutive trials from day 15 was combined, control/saline, HT1001/saline and HT1001/scopolamine groups outperformed the control/scopolamine group (data not shown). In addition, with combined data, the HT1001/saline treated group took significantly less time to locate the platform than the HT1001/scopolamine treated group (data not shown). The results from day 15 indicate that scopolamine treatment produces a memory deficit and that HT1001 can offset this memory deficit.

Figure 27C:
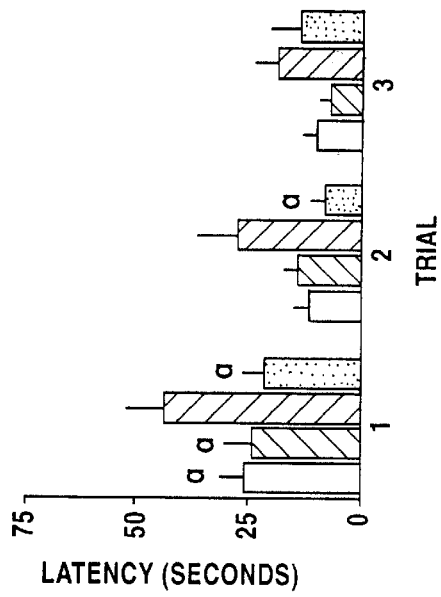

When rats were required to initially learn the second new location for the platform (day 16), significant effects were again demonstrated only during the third trial. Saline injected animals (mean latency 7.5±1.1 (23) seconds) had significantly p<0.01 latencies, compared to scopolamine treated animals (mean latency 18.4±2.9 (24) seconds). In particular, control/saline and HT1001/saline treated animals outperformed control/scopolamine animals (FIG. 27c).

Figure 27D:
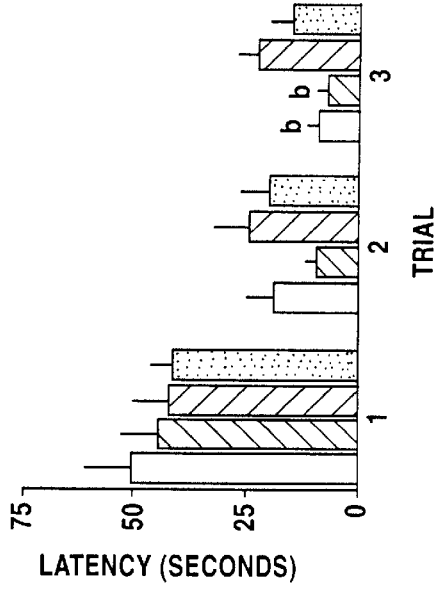

When the rats were required to demonstrate that they remembered the new location of the platform on the following day (day 17), control/scopolamine treated rats exhibited a memory defici.t on the first trial (FIG. 27d). In addition, HT1001/saline treated animals outperformed the control/scopolamine animals in the second trial (FIG. 27d). When the data from the three consecutive trials from day 17 was combined, control/saline, HT1001/saline and HT1001/scopolamine groups outperformed the control scopolamine group (data not shown). The results from day 17 indicate that scopolamine treatment produces a memory deficit and that pretreatment with HT1001 offsets the scopolamine effect such that HT1001/scopolamine, HT1001/saline and control/saline animals performed the task with identical facility.

We also studied the effects of HT1001 on choline uptake in synaptosomes. Ginsenoside Rb1 has been demonstrated to increase choline uptake (Benishin, Neurochem. Int. 21: 1–5 (1992)), A decrease in the production of the neurotransmitter acetylcholine is associated with memory loss and Alzheimer's disease. Rb1 has been demonstrated to increase choline uptake into neurons and this, presumably, enhances MS acetylcholine production which, in turn, alleviates memory impairment. In order to show that HT1001 has properties which alleviate memory loss, we wanted to establish that HT1001 increases choline uptake in nervous tissue preparations.

We have examined choline uptake in synaptosome preparations from whole brain and hippocampus in the presence of Rb1, HT1001 and HC3. Rb1 is a positive control as it has been previously demonstrated to increase choline uptake into synaptosomes whereas HC3 is a negative control which is known to inhibit choline uptake.

Figure 28:
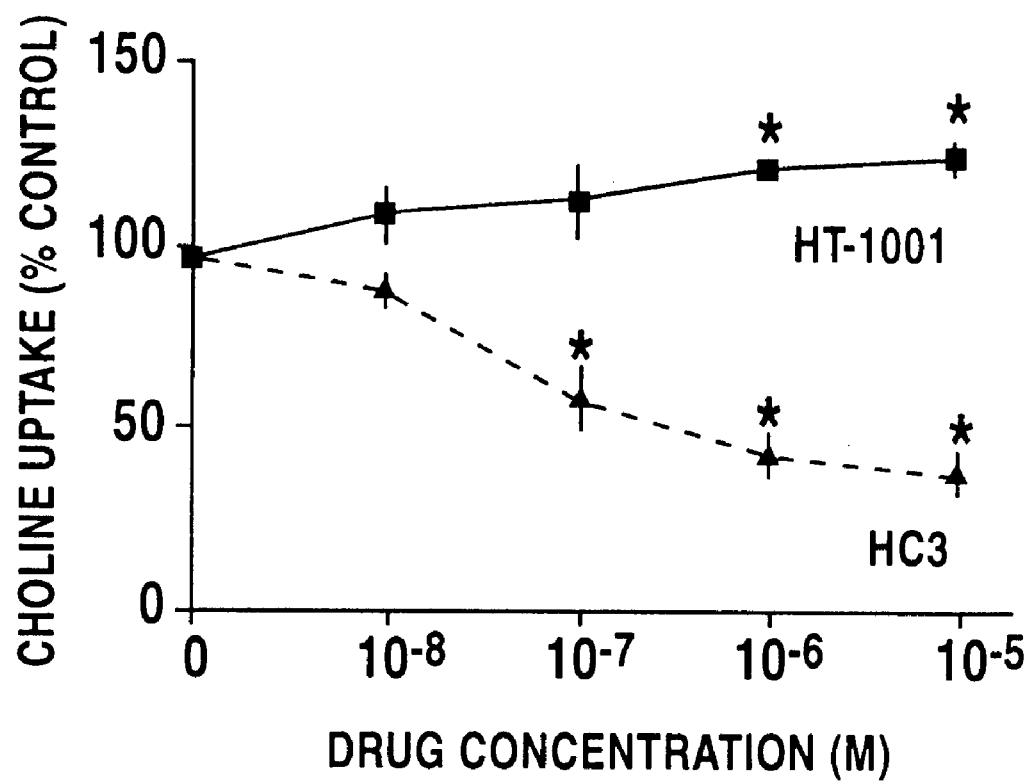
FIG. 28 shows the effects of various doses of HT1001 and HC3 on choline uptake by rat brain synaptosomes.

FIG. 28 demonstrates the effects of various doses of HT1001 and HC3 on choline uptake by rat brain synaptosomes (the asterisk * indicates that the treatment is significantly different from controls, p<0.05, n=10). This study indicates that our synaptosome preparations are viable, that HT1001 promotes choline uptake and that HC3 inhibits choline uptake as has been previously demonstrated (Benishin, 1992). The magnitude of these effects are consistent with the previous studies.

Experiments using both Rb1 and HT1001 indicate that our materials increase choline uptake into synaptosomes derived from the rat hippocampus and whole brain (Table 5). HT1001 at a concentration approximating $1 \times 10^{-6}$ M saponins (molecular weight was established at 900) was always effective in promoting choline uptake. A higher dose ($1 \times 10^{-5}$ M) was not always effective. This observation is not unexpected, as many pharmacological compounds have an optimal dose range and more or less of the material results in less biological activity. Certain compounds which are antagonistic to Rb1 found in HT1001 could inhibit choline uptake at higher doses of HT1001.

TABLE 5

Effects of Rb1 and HT1001 on choline uptake into synaptosomes prepared from rat hippocampus.

| Experiment Number | Tissue | HT1001 $1 \times 10^{-6}$M % control | HT1001 $1 \times 10^{-6}$M % control | Rb1 $1 \times 10^{-6}$M % control |
| --- | --- | --- | --- | --- |
| 1 | Hippocampus | 116* | 123* | 126* |
| 2 | Hippocampus | 100 | 113* | 111* |
| 3 | Hippocampus | 102 | 121* | 125* |
| 4 | Whole Brain | 102 | 110* | N.D. |
| 5 | Whole Brain | 110 | 119* | N.D. |

Values are the mean percent increase in uptake of radioactive choline.
*significantly different from controls p < 0.05 (ANOVA, Student/Newman/Kuels). N.D. not done. Sample sizes for experiments 1–3 n = 10, experiments 4, 5 n = 6.

We also studied the immunostimulatory effects of HT1001. Ginseng is noted for its ability to stimulate the immune system. This stimulation is often associated with the oligosaccharide components of the ginseng. However, as HT1001 does contain some oligosaccharides and as ginsenosides contain saccharide constituents which are released upon digestion, it may be that HT1001 can also stimulate the immune system. In order to test this theory, mice fed HT1001 were be evaluated for immunological responses.

As can be seen in Table 6, HT1001 administered by gavage in either corn oil or water had no effect on serum IgG concentrations in mice fed the material for 4 days. Ginseng essence administered in corn oil also had no effect on serum IgG concentrations. These results indicate that HT1001 does not possess the immune system stimulating properties found in other ginseng preparations.

TABLE 6

Effects of HT1001 and Ginseng Essence on Serum IgG levels in mice fed 200 mg/kg/day for 4 days in oil suspensions.

| Treatment | Response (% control) |
| --- | --- |
| Control (200 µl corn oil/day, 4 days) | 100 ± 13 |
| HT1001 (200 mg/kg/day, 4 days) | 103 ± 9 |
| Ginseng Essence (200 mg/kg/day, 4 days) | 106 ± 12 |
| Control (200 µl water/day, 4 days) | 100 ± 9 |
| HT1001 (200 mg/kg/day, 4 days) | 106 ± 11 |

Values are the means ± the standard deviations based on a sample size of 10. No significant differences were determined.

We also studied the effects of HT1001 on aminergic neurotransmitters. Aminergic neurotransmitters have a large number of physiological properties. These neurotransmitters are involved in immunological responses, depression, impotence, premenstrual syndrome, schizophrenia and Parkinson's disease. Loss of neurons containing these neurotranmitters is a general manifestation of aging. Drugs which increase the activity of aminergic neurotransmitter systems are commonly used to alleviate these disorders. For example PROZAC and Deprenyl, which selectively increase the activity of certain of these aminergic neurotransmitter systems, are used to treat depression, impotence and Parkinson's disease. The demonstration of similar properties associated with HT1001 would indicate that this product is suitable for the treatment of the aforementioned diseases.

Previous studies (Zhang et al, *Chinese Med. J.* 103: 932–938 (1990)) have claimed that treatment with ginsenosides Rb1 and Rg1, decrease the levels of the aminergic neurotransmitter 5-hydroxytryptamine (serotonin) and its metabolite 5-hydroxyindoleacetic acid in rat and mouse brain. Unfortunately, the levels reported for 5-hydroxytryptamine and 5-hydroxyindoleacetic acid in the study by Zhang et al (1990) are at least 50 times the usually reported levels. In order to provide valid information, we conducted our own studies on HT1001 and aminergic neurotransmitter levels in mice. Ginseng essence, which is water insoluble, as well as HT1001, was administered in corn oil.

As can be seen in Table 7, the oral administration of HT1001 in corn oil significantly elevated 5-HT concentrations in the mouse brain. This elevation of 5-HT levels following HT1001 administration is promising and may suggest an increase in the activity of the 5-HT neurotransmitter system. This would be consistent with an antidepressant effect for HT1001.

TABLE 7

Concentrations of the aminergic neurotransmitters noradrenaline (NA), dopamine (DA), 5-hydroxytryptamine (5-HT) and the metabolites dihydroxyphenyl acetic acid (DOPAQ) and 5-hydroxyindoleacetic acid (5-HIAA in the brains of mice fed either HT1001 or ginseng essence.

| Treatment | NA ng/g | DA ng/g | 5-HT ng/g | DOPAC ng/g | 5-HIAA ng/g |
|---|---|---|---|---|---|
| Control (200 μl corn oil/day, 4 days) | 381 ± 18 | 1918 ± 69 | 805 ± 13 | 82 ± 6 | 174 ± 10 |
| HT1001 (200 mg/kg/day, 4 days) | 408 ± 4 | 2055 ± 62 | 955 ± 40* | 79 ± 4 | 205 ± 11 |
| Ginseng essence (200 mg/kg/day, 4 days) | 416 ± 18 | 1851 ± 141 | 848 ± 43 | 69 ± 9 | 195 ± 9 |

Values are the mean ± the standard deviation based on 5 determinations. HT1001 and ginseng essence were administered in a volume of 200 μl corn oil. *Statistically significant elevation p < 0.05 (ANOVA).

As a result of this initial study, we have concentrated on HT1001 treatments and have completed an experiment where mice received HT1001 dissolved in water (200 mg/kg/day, 6 days) and have examined two regions of the brain (hypothalamus/hippocampus and rest of the brain).

Tables 8 and 9 indicate that no effects of HT1001 on aminergic neurotransmitters are evident when mice are fed HT1001 in water for 6 days. It is possible that administering HT1001 in corn oil rather than water promotes absorption of ginsenosides or that the difference in treatment duration affects the results. This study has now been repeated using corn oil as a carrier (Table 10). Unfortunately, no significant effects were noted, although 5-hydroxyindoleacetic acid and dihydroxyphenyl acetic acid levels appeared somewhat elevated, suggesting a possible increase in neurotransmitter turnover.

TABLE 8

Concentrations of the aminergic neurotransmitters noradrenaline (NA), dopamine (DA), 5-hydroxytryptamine (5-HT) and the metabolites dihydroxyphenyl acetic acid (DOPAC) and 5-hydroxyindoleacetic acid (5-HIAA) in the hypothalamus/hippocampus of mice fed HT1001.

| Treatment | NA ng/g | DA ng/g | 5-HT ng/g | DOPAC ng/g | 5-HIAA ng/g |
|---|---|---|---|---|---|
| Control (200 μl water/day, 6 days) | 606 ± 28 | 965 ± 124 | 791 ± 28 | 124 ± 10 | 304 ± 17 |
| HT1001 (200 mg/kg/day, 6 days) | 567 ± 31 | 876 ± 161 | 869 ± 35 | 118 ± 15 | 326 ± 15 |

Values are the mean ± the standard deviation based on 10 and 9 determinations. HT1001 and ginseng essence were administered in a volume of 200 μl water.

TABLE 9

Concentrations of the aminergic neurotransmitters noradrenaline (NA), dopamine (DA), 5-hydroxytryptamine (5-HT) and the metabolites dihydroxyphenyl acetic acid (DOPAC) and 5-hydroxyindoleacetic acid (5-HIAA) in the rest of the brain of mice fed HT1001.

| Treatment | NA ng/g | DA ng/g | 5-HT ng/g | DOPAC ng/g | 5-HIAA ng/g |
|---|---|---|---|---|---|
| Control (200 μl water/day, 6 days) | 319 ± 14 | 1130 ± 49 | 737 ± 29 | 43 ± 5 | 239 ± 21 |
| HT1001 (200 mg/kg/day, 6 days) | 311 ± 11 | 1294 ± 68 | 779 27 | 56 ± 5 | 240 ± 16 |

Values are the mean ± the standard deviation based on 10 determinations. HT1001 and ginseng essence were administered in a volume of 200 μl water.

TABLE 10

Concentrations of the aminergic neurotransmitters noradrenaline (NA), dopamine (DA), 5-hydroxytryptamine (%-HT) and the metabolites dihydroxyphenyl acetic acid (DOPAC) and 5-hydroxyindoleacetic acid (5-HIAA) in the brains (transverse slices containing hypothalamus, striatum, hippocampus and some cortex) of mice fed HT1001.

| Treatment | NA ng/g | DA ng/g | 5-HT ng/g | DOPAC ng/g | 5-HIAA ng/g |
|---|---|---|---|---|---|
| Control (200 μl water/day, 6 days) | 515 ± 27 | 1354 ± 105 | 622 ± 28 | 108 ± 7 | 204 ± 10 |
| HT1001 (200 mg/kg/day, 6 days) | 501 ± 15 | 1497 ± 127 | 619 ± 14 | 128 ± 10 | 222 ± 5 |

Values are the mean ± the standard deviation based on 10 determinations. HT1001 was administered in a volume of 200 μl corn oil. No statistically significant differences are noted.

In order to maximize the use of animals employed in the learning behavior experiment, we also examined these animals for possible effects of HT1001 on aminergic neurotransmitter metabolism. Table 11 indicates the concentrations of a number of aminergic neurotransmitters and their metabolites in several regions of the brains of control and HT1001 fed rats. No significant differences were determined.

TABLE 11

Concentrations of the aminergic neurotransmitters noradrenaline (NA), dopamine (DA), 5-hydroxytryptamine (5-HT) and the metabolites dihydroxyphenyl acetic acid (DOPAC) and 5-hydroxyindoleacetic acid (5-HIAA) in various regions of the brains of rats fed HT1001 (200 mg/kg/day, 17 days).

| Brain Region | Treatment | NA ng/g | DA ng/g | 5-HT ng/g | DOPAC ng/g | 5-HIAA ng/g |
|---|---|---|---|---|---|---|
| Hypothalamus | Control | 300 ± 11 | 119 ± 13 | 668 ± 27 | 76 ± 6 | 204 ± 10 |
|  | HT1001 | 302 ± 26 | 100 ± 8 | 652 ± 42 | 68 ± 7 | 195 ± 16 |
| Striatum | Control | 375 ± 26 | 1760 ± 194 | 639 ± 29 | 401 ± 62 | 429 ± 18 |
|  | HT1001 | 419 ± 19 | 1662 ± 100 | 672 ± 19 | 346 ± 20 | 456 ± 21 |
| Cortex | Control | 69 ± 5 | 241 ± 65 | 234 ± 18 | 84 ± 11 | 119 ± 7 |
|  | HT1001 | 80 ± 6 | 410 ± 145 | 235 ± 59 | 108 ± 12 | 124 ± 25 |

Values are the mean ± the standard deviation based on 6 determinations except HT1001 cortex (5 determinations). HT1001 was administered in a volume of 500 μl water, controls received 500 μl water. No significant differences were determined.

We have also investigated the effects of HT1001 on noradrenaline, dopamine and 5-hydroxytryptamine reuptake and monamine oxidase A and B activity in vitro. When compared to amphetamine, HT1001 has little effect on noradrenaline or dopamine uptake. For example, at $10^{-4}$ M (assuming a molecular weight of 900 for HT1001) HT1001 inhibits noradrenaline uptake in hypothalamus slices 3.0% whereas amphetamine at $10^{-5}$ M inhibits uptake by 83%. In striatal slices, HT1001 ($10^{-4}$ M) inhibits dopamine uptake by 2.5% whereas amphetamine ($10^{-5}$ M) inhibits dopamine uptake by 92.4%. HT1001 has a small effect on 5-hydroxytryptamine uptake in striatal slices, where HT1001 ($10^{-4}$) inhibits uptake by 19.1% and amphetamine ($10^{-5}$ M) inhibits uptake by 94%. None of these effects are dramatic.

With respect to monoamine oxidase activity, there is again little effect by HT1001. HT1001 ($10^{-4}$ M) inhibits monoamine oxidase A activity by 5.4% whereas phenylzine ($10^{-4}$ M) inhibits monoamine oxidase A activity by 97.5%. HT1001 has a slight effect on monoamine oxidase B activity as HT1001 ($10^{-4}$ M) inhibits monoamine oxidase B activity by 18.5%. However, this is not dramatic, as phenylzine ($10^{-4}$ M) inhibits monoamine oxidase B activity by 93.0%.

We also studied the antimicrobial effects of HT1001. Ginseng has often been reported to have antimicrobial and antiviral effects. We routinely examine our extracts for microbial contamination in order to provide a safe product to the public. Our first lot of HT1001 (lot # 95-1001-001) has indicated a very low microbial count (Table 12). Thus, HT1001 has antimicrobial properties.

TABLE 12

Standard Microbial Counts Found in HT1001 and HT2001.

| Product | Microbial Count/g product |
|---|---|
| HT1001 | 40 |
| HT2001 | $8.2 \times 10^4$ |

HT1001 provides a water soluble, concentrated preparation of ginsenosides. HT1001 provides 3.4 times the concentration by weight of ginsenosides than does root powder. Evidence indicates that HT1001 can improve the retention of newly learned tasks in animal models and, consistent with this idea, it can promote choline uptake. The ability of HT1001 to promote choline uptake in rat brain synaptosomes has been established, suggesting that HT1001 may be used in the treatment of Alzheimer's disease. Preliminary studies suggested that HT1001 might have effects on the 5-hydroxytryptamine neurotransmitter system and that these effects might be indicative of an antidepressant effect. Further studies did not substantiate this observation. HT1001 does not stimulate the immune system after oral administration. HT1001 has extremely low microbial counts, and this suggests potential antimicrobial properties associated with chemicals found in HT1001.

EXAMPLE 4

A study of memory in human subjects after HT1001 administration was conducted. The methods were as follows.
1. Individuals underwent a physical examination consisting of the following tests:
  A: Blood pressure (BP), mm-Hg, systolic/diastolic
  B: EKG
  C: Routine urine examination including urobilinogen, urobilirubin, occult blood, acetone bodies, glucose, protein, pH, nitrites
  D: Routine blood examination including WBC count, neutrocytes, hemoglobin, platelets
  E: Chest X-ray
  F: Liver functions including ALT (alanine transaminase), AST (aspartate transaminase)
  G: HBsAg
2. Memory tests were assessed as follows:
  Memory Quotient (MQ) measurement tables were used. There were 5 tests.
  A: Directed memory: After announcing 24 words the individual examined was asked to repeat the words grouped by categories, e.g., vegetables.
  B: Paired association memory: After announcing 12 pairs of words to the individual being examined the first word of each pair of words was repeated and the individual was asked to say the other paired word. Some pairs of words were related, such as up-down and sun-moon. Some word pairs were totally unrelated such as horse-lamp.
  C: Free recall of pictures: After being shown 15 pictures, the individual being examined was asked to recall and describe the pictures he or she had seen.
  D: Recognition of meaningless figures: 20 figures of meaningless curves were shown the individual being examined. Following this a second group of 20 figures was shown to the individual. Half of the second group of curve had been shown previously. The individual was asked to indicate which of the figures he or she had seen previously.
  E: Recall of connections with portraits: Six portraits, each with a surname, a profession, and a hobby, were shown to the individual being examined. For example, a portrait could have the surname Zhang whose profession was teacher and whose hobby was watching television. After a set period of time the portraits were shown in a different order. The individual being examined was asked to recall the features associated with each portrait.

Each test was scored and the sum for each individual examined was calculated to provide a MQ. Every individual examined was tested twice, before and after taking HT-1001 or a control diet. Each individual was subjected to a physical examination prior to and after taking HT-1001 or a control diet. The physical examinations are intended to ensure that there were no side effects associated with taking HT-1001.

The tests were performed on both a young group and an aged group. The young test group consisted of 10 university students, 5 females and 5 males, aged 20 to 24 who took HT-1001 (two 200 mg capsules per day) for 13 days. The young control group consisted of 12 individuals, 3 females and 9 males, aged 20 to 24 who consumed a placebo. The aged test group consisted of 10 individuals, 5 male and 5 female, aged 46 to 64 years who consumed HT-1001 (two 200 mg capsules per day) for 14 days. The aged control group consisted of 5 people, 2 females and 3 males, aged from 40 to 65.

A group T-test was used for comparison between control and experimental group.

Each test was scored and the sum of the score for each individual examined was calculated to provide a MQ. Each individual was tested twice, once prior to and once after consuming either control diet or HT-1001. The results are presented in the following Table 13.

TABLE 13

MQs of Young and Aged Groups Before and After Taking HT1001

| Individual | Young | | Aged | |
|---|---|---|---|---|
| | Before | After | Before | After |
| 1 | 113.5 | 138 | 91 | 98 |
| 2 | 130 | 138 | 105 | 103.5 |
| 3 | 127 | 135 | 97.5 | 129 |
| 4 | 124 | 131 | 93 | 113 |
| 5 | 118 | 131.5 | 96 | 90 |
| 6 | 119 | 135 | 95 | 109 |
| 7 | 116 | 130 | 107 | 115 |
| 8 | 118 | 133 | 105 | 130 |
| 9 | 106 | 124 | 123 | 136 |
| 10 | 114 | 127 | 114 | 109 |

MQ is calculated by an equation from the scores and is divided into 7 grades. MQ > 130 is the first grade (above excellent); 129–120 is the second grade (excellent); 119–110 (good); 109–90 (middle); 89–80 (fair); 79–70 (poor); 69–60 (bad).

TABLE 14

Difference of MQ Between Control and HT1001-Treated Groups of Young People.

| People | Control 12 | HT1001 10 |
|---|---|---|
| Test A | 3.8 ± 3.2 | 3.9 ± 3.1 |
| Test B | 1.9 ± 4.7 | 4.2 ± 3.8 |
| Test C | 3.2 ± 5.5 | 3.8 ± 5.1 |
| Test D | −3.0 ± 5.6 | 3.2 ± 3.3** |
| Test E | −0.7 ± 4.1 | 1.7 ± 2.9 |
| Sum | 5.3 ± 11.4 | 18.8 ± 7.4** |
| MQ | 3.7 ± 8.1 | 13.7 ± 5.3** |

Values are the means ±SD. **$P < 0.01$ in comparison with control. The values in tests A–E represent the difference of the scores before and after taking the control diet or HT-1001.

TABLE 15

Difference of MQ Between Control and HT1001-Treated Groups of Aged People.

| People | Control 5 | HT1001 10 |
|---|---|---|
| Test A | 2.6 ± 2.4 | 6.4 ± 5.0 |
| Test B | −0.3 ± 2.1 | 5.2 ± 3.6** |
| Test C | 2.8 ± 2.4 | −1.3 ± 5.0 |

TABLE 15-continued

Difference of MQ Between Control and HT1001-Treated Groups of Aged People.

| People | Control 5 | HT1001 10 |
|---|---|---|
| Test D | −7.3 ± 4.9 | 3.2 ± 3.7** |
| Test E | −4.8 ± 6.4 | −2.2 ± 5.9 |
| Sum | −6.6 ± 9.7 | 12.6 ± 15.3* |
| MQ | −5.6 ± 8.4 | 10.5 ± 12.8* |

Values are the means ±SD. *$P < 0.05$, **$P < 0.01$ in comparison with control. The values in tests A–E represent the difference of the scores before and after taking the control diet or HT-1001.

Table 13 shows that of the 10 young people examined 9 had their MQ upgraded after taking HT-1001 whereas on person (individual #2) retained the same MQ. Individual #5 had the MQ increased by 2 grades. In the aged group 5 of the 10 people examined had their MQ increased by at least 1 grade (one of these people had the MQ increased by 2 grades) following HT-1001 treatment. Four people received the same grade and one person received one grade lower following HT-1 001 treatment.

Tables 14 and 15 indicate there is a significant increase in MQ scores with HT-1001 treated people (both young and aged) when compared with controls. In the young group there is a significant overall increase in the MQ score associated with HT-1001 consumption. Test D, in particular, resulted in a significant increase in score associated with HT-1001 treatment. In the aged group there was a significant overall increase in the MQ score associated with HT-1001 treatment. Tests B and D, in particular, demonstrated significant improvement with HT-1001 treatment. Test B is a test of language retention whereas test D is a non-verbal memory test.

EXAMPLE 5

A study of the neurotrophic effects of HT1001 and some pure ginsenosides was conducted. A new mechanism of action for HT1001 was shown, which is the stimulation of neurite outgrowth in a PC12 cell line. This research indicates that HT1001 may not only act to alleviate symptoms, but may alter the progression of neurodegenerative diseases. The beneficial effects (prevention/treatment) of HT-1001 may apply to degenerative diseases such as senile dementia, Parkinson's disease, Alzheimer's disease, multi-infarct dementia, etc.

Alzheimer's disease (AD) is associated with degeneration of cholinergic nerve tracts including projections from the basal forebrain to the cortex and hippocampus. The PC12 (pheochromocytoma) cell line is one of the models for the study of the development of these nerve tracts. The cell line is phenotypically a chromaffin cell line, but can be induced to express adrenergic and cholinergic markers as well. This model has the advantages that (1) it is an immortalized cell line, (2) it is sensitive to, but not dependent upon, NGF for survival, and (3) it shares many properties in common with the central cholinergic neurons of the basal forebrain. It has been noted that PC12 cells are not sensitive to all of the trophic factors that central cholinergic neurons respond to, whereas central cholinergic neurons respond to all trophic factors that PC12 cells respond to. For this reason the PC12 cell line can be viewed as an ideal model system which is unlikely to provide false positive results although it may give false negative results, i.e., it may be possible to miss a trophic factor which is acting on central cholinergic neuron.

PC12 cells have been reported to respond to NGF in many ways, including, but not limited to, the following: development of membrane excitability, synthesis, assembly and stabilization of cytoskeletal structures, increased cell adhesion, hypertrophy and increased anabolic activity, decreased DNA synthesis and cellular proliferation; selective induction of antioxidant (e.g. catalase) and energy metabolism enzymes; stimulation of cholinergic neurotransmitter metabolism (e.g. CHAT activity; altered gene expression; increased neurite outgrowth; increased expression of surface membrane receptors; increased expression of APP-695 (which is important with respect to the etiology of Alzheimer's Diseases; increased expression of omega-CgTx sensitive $Ca^{2+}$ channels; increased expression of zeta-PKC, down-regulation of other isoforms of PKC leading to enhancement of neurite outgrowth. Because PC12 cells respond to NGF with a variety of documented responses, they are likely candidates for studying the NGF-like properties of other substances. They support the notion that these cells are a good model for central cholinergic nerons of the basal forebrain.

PC12 cells were seeded and maintained in 100 cm² tissue culture dishes at 37° C. in RRMI1640 containing 1% antibiotics, 10% heated inactivated horse serum and 5% fetal bovine serum in a water saturated atmosphere of 95% air and 5% $CO_2$. The cells were mechanically dislodged for experiment by forceful aspiration of medium through a Pasteur pipette and plated into 35 mm collagen-coated tissue culture dishes containing a total of 2.0 ml of complete medium at a density of $1\times10^4$ cells/ml. The medium was changed 3 times per week.

The cellular responses to Nerve Growth Factor (NGF) and samples were determined by counting the number of cells containing processes in PC12 cells. Photographs of the cells were taken seven and 14 days of treatment. Two fields were chosen in every dish and then the films were developed and printed. The cells and neurites were counted as follows: The cells with circular or global shape and no neurite outgrowth were scored as 0 (S0). The cells which became elongated or showed short neurite outgrowth were scored as S1. Cells with more than two small neurites on the cell bodies were scored as S2. Cells with one or two neurites with a length of at least two times diameter as their body were scored as S3. Cells with more than two long neurites were scored as S4. The neurite index was calculated as below:

Neurite index (In)=total neurite Score (ΣS)/total cell number (ΣN)

ΣS=S1×N+S2×N+S3×N+S4×N; N is the cell number of every cell field.

The test samples included: NGF, HT1001, PQ4, PQ5, PQ6, Rb1 and Rg1

Figure 29:
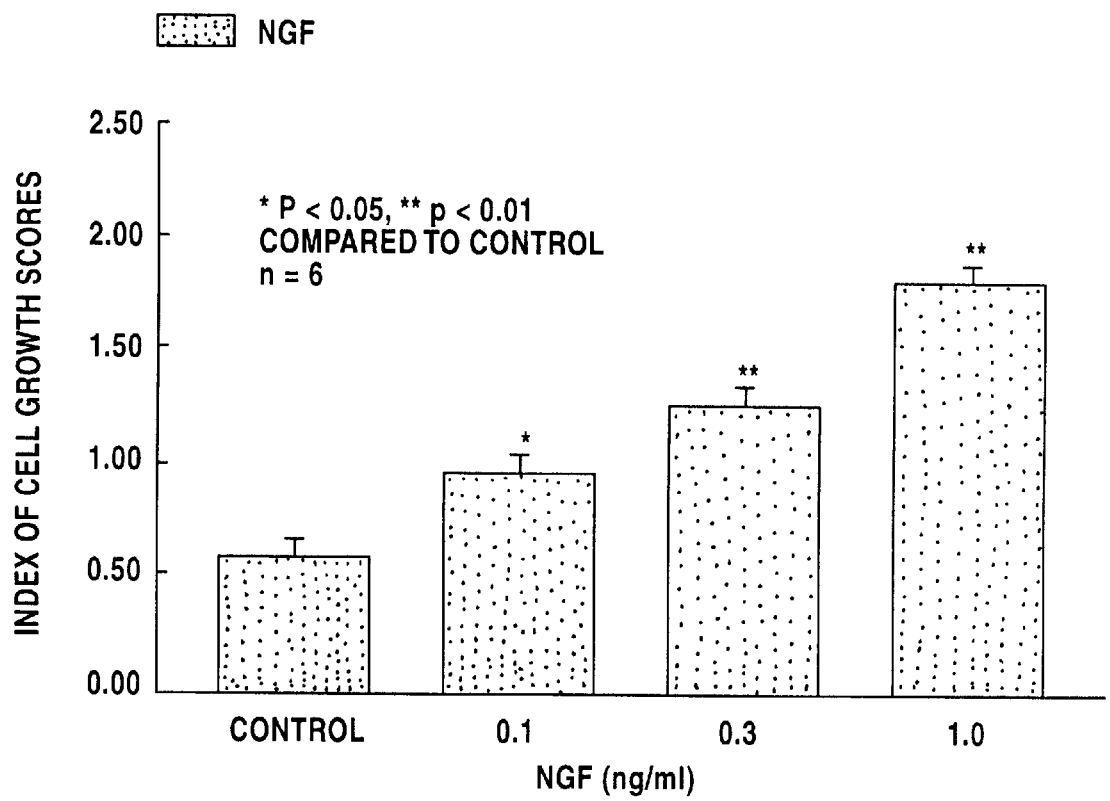
FIGS. 29–31 show results for tests of neurite outgrowth in PC12 cells using various products.

NGF increased neurite outgrowth in PC12 cells in a dose-dependent manner seven days after treatment (FIG. 29).

Figure 30:
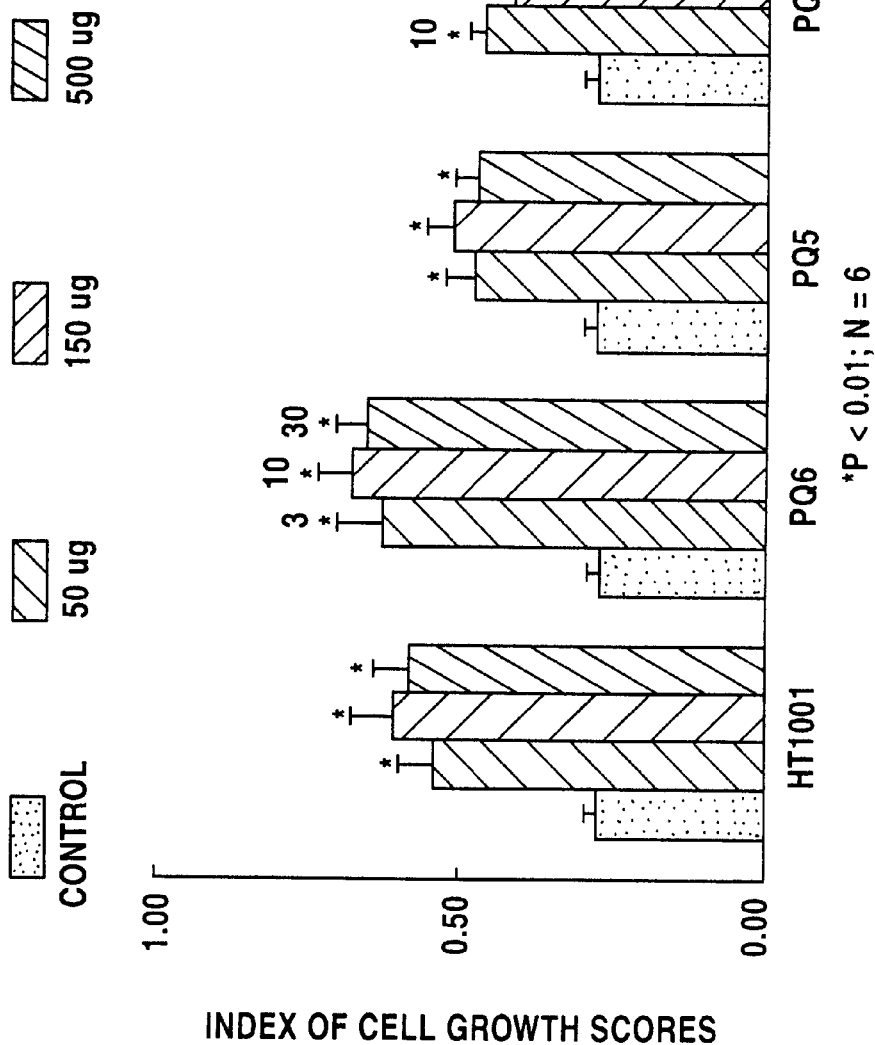

HT1001, PQ4, PQ5 and PQ6 significantly increased neurite outgrowth in PC12 cells seven days after treatment (FIG. 30). Doses applied were 50, 150 and 500 μg/ml for HT1001 and PQ5; 10, 50 and 150 μg/ml for PQ4; and 3, 10 and 30 μg/ml for PQ6.

Figure 31:
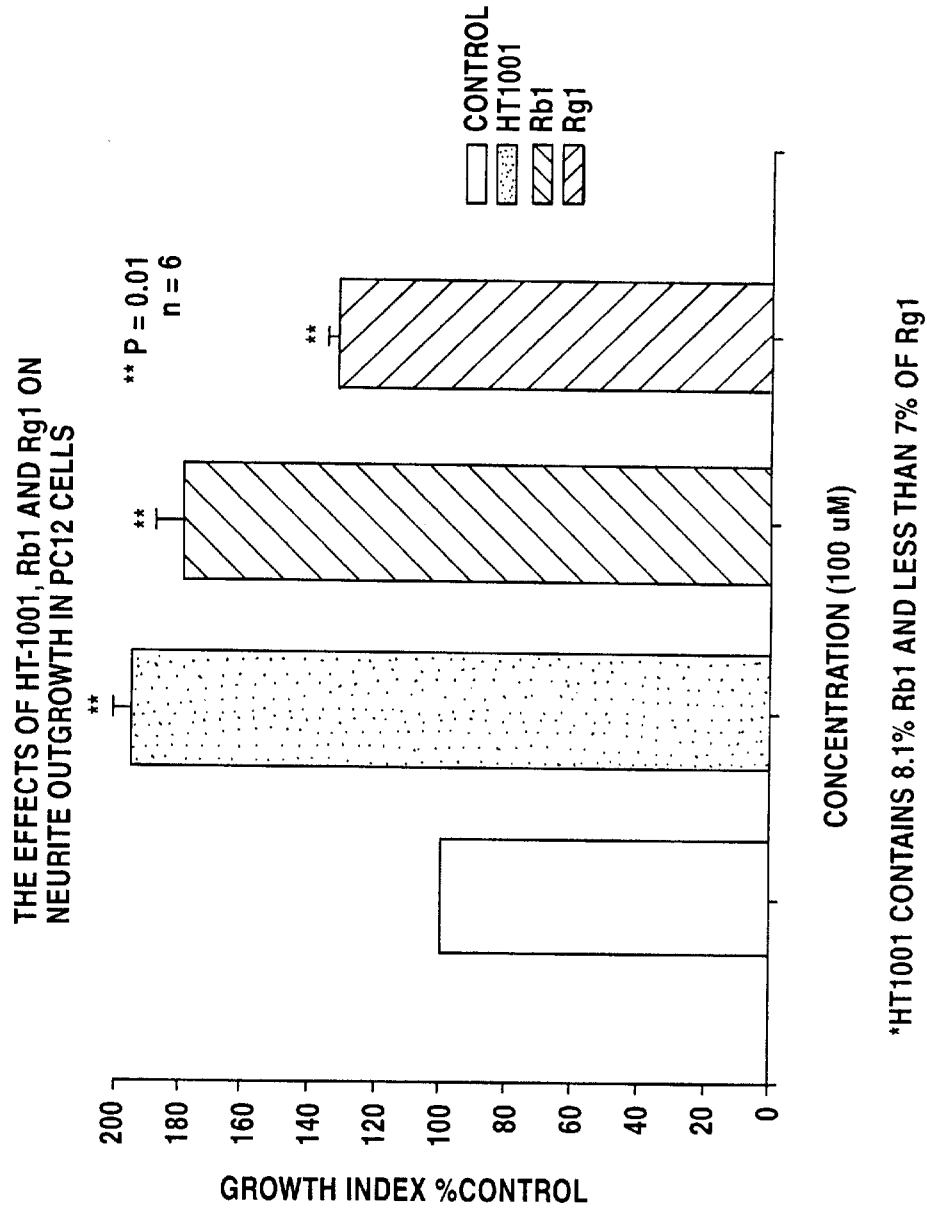

HT1001, Rb1 and Rg1 significantly increased neurite outgrowth in PC12 cells seven days after treatment (FIG. 31). At the same concentration, HT1001 produced a similar effect as Rb1 and a more pronounced effect than Rg 1.

HT1001 caused a NGF-like effect in stimulating neurite outgrowth in PC12 cell lines. This may contribute to its beneficial effect in the treatment and prevention of neurodegenerative diseases. The effect of HT1001 seemed to be the same as PQ4, PQ5 and PQ6 at the same doses. The results also demonstrated that at the same dose, HT1001 produced the same effect as Rb1 and had a better effect than Rg1.

EXAMPLE 6

A study of the effects of HT1001 and some pure ginsenosides on calcium channel activity in cultured neuroblastoma cells was conducted.

Recently, a hypothesis of cellular calcium homeostasis has been introduced as a mechanism involved in understanding brain aging and neurodegenerative disorders (Siesjo, Ann. N.Y. Acad. Sci. 747: 140–161 (1994); Khachaturian, Ann. N.Y. Acad. Sci. 747: 1–11 (1994)). This hypothesis suggested that a sustained disturbance in cellular calcium homeostasis may be the ultimate pathway for the neuropathological changes associated with brain aging and various neurodegenerative disorders. Evidence shows that neuronal aging and dementia are associated with elevated levels of free intracellular $Ca^{2+}$, defects in plasma membrane calcium transport activity (Michaelis et al, 1996) and increased calcium channels (Landfield, 1996). The calcium theory was further supported by some positive results concerning calcium channel blockers which improved learning and memory.

Neuroblastoma Cell Culture. Mouse neuroblastoma cells (N1E115) were cultured in Dulbecco's modified Eagle's medium (GIBCO) containing 10% fetal bovine serum at 37° C. in a humidified atmosphere of 5% $CO_2$ in air. The medium was changed every 3–4 days. After mechanical agitation, $3\times10^4$ cells were replanted in 35 mm tissue culture dishes containing 4 ml of bath solution. After cell attachment, the dish was mounted on the stage of an inverted phase-contrast microscope (Nikon) for $Ca^{2+}$ channel current recording. These cells expressed predominately T channel currents. In experiments where L channels were specifically sought, the cells were grown and maintained at confluence for 3–4 weeks under the same culture conditions with the addition of 2% (vol/vol) dimethyl sulfoxide. Three to five days before use, the cells were replanted with the same medium. These cells expressed predominately L channel currents. A small number of these cells also expressed T channel currents. Hence, cells were selected so that at a holding potential of −40 mV, the T channel component, was very small and the inward current measured was conducted predominantly by L channels.

$Ca^{2+}$ Channel Current Recording in Neuroblastoma Cells. The whole-cell variation of the patch-clamp technique was used. The pipettes had resistance of 2–15 MΩ. Membrane current recordings were made with an Axopatch-1C (Axon Instruments) patch-clamp amplifier. All signals were filtered at 1 kHz and stored in the computer. Since the peak currents measured with 20 mM $Ba^{2+}$ as the charge carrier were usually small (about 200 pA) the series resistance compensation was not usually employed. If the capacitive transient overlapped with the onset of the inward current, or if the spatial voltage control was inadequate (i.e., NIE-115 cells with long neural outgrowths), the experimental data were rejected. Unless otherwise specified the current-voltage plots were constructed by using the peak values (corrected for leakage) from the original records for both T and L channel currents. The holding membrane potential was fixed at −80 mV when the T channels were under investigation, or at −40 mV when the L channels were studied. $Ba^{2+}$ currents through $Ca^{2+}$ channels were elicited by 200 msec depolarization at intervals of 5 sec. For every single-cell recording, stable readings were first obtained for 5 min; the drug was then added to the bath solution. Experiments were performed at room temperature(21–22° C.) to prolong cell survival and channel recording time. The bath solution contained 110 mM Tris, 5 mM KCl, 5 mM CsCl, 20 mM Hepes, 30 mM glucose, 20 mM $BaCl_2$, and 0.5 μM tetrodotoxin.

The pipette (internal) solution contained 70 mM $Cs_2$-aspartame, EGTA 10, 2 mM ATP-$Na_2$, 5 mM K-pyruvate, 5 mM K-succinate, 5 mM Phosphocreatine-$Na_2$, 15 units/ml Creatine kinase, Hepes and 5 mM glucose. The osmolality of all solutions was adjusted to 310–320 mOsm and pH to 7.4 using HCl or CsOH as required.

Figure 32:
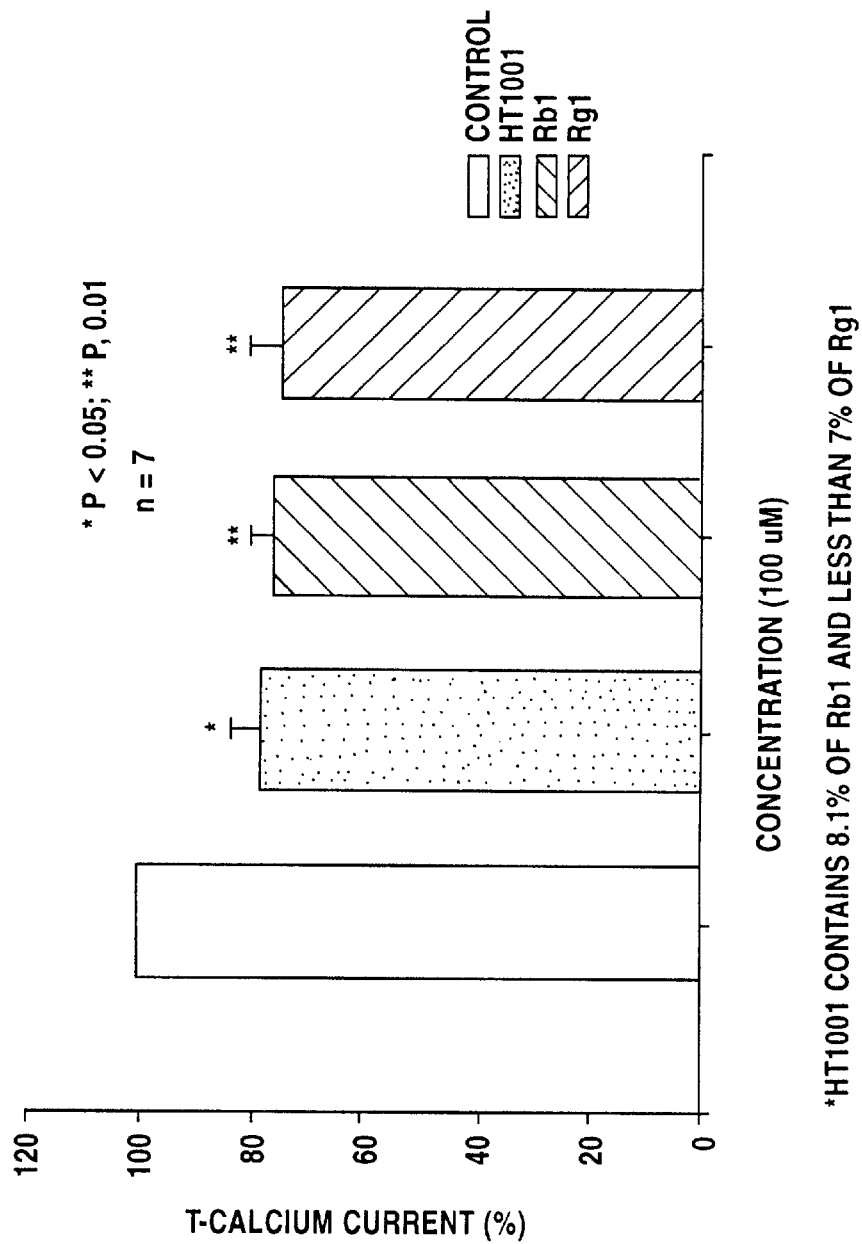

FIG. 32 shows that, at the same concentration, HT1001, Rb1 and Rg1 produce a significant inhibitory effect on T type calcium channel currents. The effects of all three samples are similar.

FIG. 33 shows that, at the same concentration, HT1001, Rb1 and Rg1 produce a significant inhibitory effect on L type calcium channel currents. The effects of all three samples are similar.

This study shows that HT1001, Rb1, and Rg1 have inhibitory effects on both T- and L-type calcium channel activity on N1E-115 cells, which may indicate neuroprotective effects. At the same dose (100 μM), all three samples produced similar effects. However, HT1001 contains only approximately 5–10% Rb1 and 3–8% Rg1.

We claim:

1. A ginseng extract, comprising a total saponin fraction which is about 20–50% by weight of the ginseng extract, and an oligosaccharide fraction which is about 40–60% by weight of the ginseng extract.

2. The ginseng extract of claim 1, further comprising an essential oil fraction which is about 4–9% by weight of the ginseng extract.

3. The ginseng extract of claim 1, wherein the total saponin fraction comprises about 3–8% Rg1+Re, about 5–10% Rb1, about 1–8% Rd and about 2–8% Rc.

4. The ginseng extract of claim 3, wherein the total saponin fraction comprises about 25–40% by weight of the ginseng extract.

5. A pharmaceutical composition, comprising the ginseng extract of claim 1 in combination with a pharmaceutically acceptable carrier.

6. A pharmaceutical composition, comprising the ginseng extract of claim 2 in combination with a pharmaceutically acceptable carrier.

7. A pharmaceutical composition, comprising the ginseng extract of claim 3 in combination with a pharmaceutically acceptable carrier.

8. A method of treating a brain condition selected from the group consisting of senile dementia, Parkinson's disease, attention deficit disorder and stroke, in a patient in need thereof, comprising administering to the patient a brain condition treating-effective amount of the ginseng extract of claim 1.

9. A method of treating a brain condition selected from the group consisting of senile dementia, Parkinson's disease, attention deficit disorder and stroke, in a patient in need thereof, comprising administering to the patient a brain condition treating-effective amount of the ginseng extract of claim 2.

10. A method of treating a brain condition selected from the group consisting of senile dementia, Parkinson's disease, attention deficit disorder and stroke, in a patient in need thereof, comprising administering to the patient a brain condition treating-effective amount of the ginseng extract of claim 3.

11. A method of treating depression in a patient in need thereof, comprising administering to the patient a depression treating-effective amount of the ginseng extract of claim 1.

12. A method of treating depression in a patient in need thereof, comprising administering to the patient a depression treating-effective amount of the ginseng extract of claim 2.

13. A method of treating depression in a patient in need thereof, comprising administering to the patient a depression treating-effective amount of the ginseng extract of claim 3.

14. A method of improving learning ability or memory in a patient in need thereof, comprising administering to the patient a learning ability or memory improving-effective amount of the ginseng extract of claim 1.

15. A method of improving learning ability or memory in a patient in need thereof, comprising administering to the patient a learning ability or memory improving-effective amount of the ginseng extract of claim 2.

16. A method of improving learning ability or memory in a patient in need thereof, comprising administering to the patient a learning ability or memory improving-effective amount of the ginseng extract of claim 3.

* * * * *

UNITED STATES PATENT AND TRADEMARK OFFICE
CERTIFICATE OF CORRECTION

PATENT NO. : 6,083,932

DATED : July 4, 2000

INVENTOR(S) : Peter PANG et al.

It is certified that error appears in the above-identified patent and that said Letters Patent is hereby corrected as shown below:

On the title page, under "Other Publications", 3rd line from the bottom in the first column, "Battacharya" should be "Bhattacharya"

In figures 2,3,21, and 24, "Linolcic acid" should read LINOLEIC acid

Column 4, line 16: 170 to 171 should read "170-179"

Column 7, line 1: gelatine should not have an "e"

Column 7, line 63: "pheneizine" should be "phenelzine"

Column 8, line 41: "Rcl" should be "Rc"

Column 10, line 41: "exeept" should read "except"

Column 11, line 34: "defici.t" should read deficit"

Column 18, line 16: "whereas on" should be "whereas one"

Signed and Sealed this

Eighth Day of May, 2001

Attest:

NICHOLAS P. GODICI

Attesting Officer

Acting Director of the United States Patent and Trademark Office